(12) United States Patent
Pepin et al.

(10) Patent No.: US 10,307,594 B2
(45) Date of Patent: Jun. 4, 2019

(54) ANALOG FRONT-END CIRCUITRY FOR BIPHASIC STIMULUS SIGNAL DELIVERY FINDING USE IN NEURAL STIMULATION

(71) Applicant: University of Washington, Seattle, WA (US)

(72) Inventors: Eric Pepin, Seattle, WA (US); Jacques Christophe Rudell, Seattle, WA (US)

(73) Assignee: University of Washington, Seattle, WA (US)

( * ) Notice: Subject to any disclaimer, the term of this patent is extended or adjusted under 35 U.S.C. 154(b) by 223 days.

(21) Appl. No.: 15/186,170

(22) Filed: Jun. 17, 2016

(65) Prior Publication Data

US 2016/0367813 A1    Dec. 22, 2016

Related U.S. Application Data

(60) Provisional application No. 62/181,046, filed on Jun. 17, 2015.

(51) Int. Cl.
*A61N 1/00* (2006.01)
*A61N 1/36* (2006.01)
(Continued)

(52) U.S. Cl.
CPC ....... *A61N 1/36125* (2013.01); *A61N 1/0529* (2013.01); *A61N 1/0551* (2013.01);
(Continued)

(58) Field of Classification Search
CPC ............ A61N 1/36139; A61N 1/36125; A61N 1/37205; A61N 1/37211; A61N 1/0551; A61N 1/36157; A61N 1/0529
See application file for complete search history.

(56) References Cited

U.S. PATENT DOCUMENTS 5,154,172 A    10/1992 Terry, Jr. et al.
6,996,435 B2    2/2006 Fassio
(Continued)

OTHER PUBLICATIONS

Arfin, et al., "An Energy-Efficient, Adiabatic Electrode Stimulator with Inductive Energy Recycling and Feedback Current Regulation", IEEE Transactions on Biomedical Circuits and Systems, vol. 6, No. 1, pp. 1-14 (Feb. 2012).
(Continued)

*Primary Examiner* — Mallika D Fairchild
(74) *Attorney, Agent, or Firm* — Dorsey & Whitney LLP

(57) ABSTRACT

Front-end analog circuitry is described based on a sink-regulated H-bridge topology for delivery of biphasic stimulus signals that may be useful in neurostimulation. Stimulus current may be supplied using fully-integrated dynamic voltage supplies (DVSs), which may be controlled in closed-loop to have an output voltage approximately equal to the voltage of the electrode each supplies stimulus to. The stimulus waveform may be regulated by a single, low-voltage current-digital-to-analog converter (current-DAC), which can safely interface with the electrodes (which may be at high voltages) via high-voltage adapter (HVA) circuits. Example analog front-end circuitry may utilize the balancing stimulus current to discharge the electrode-tissue interface impedance ($Z_E$). In some examples, only after full (or sufficient) $Z_E$ discharge has been detected is a DVS used to supply the remaining balancing stimulus.

12 Claims, 8 Drawing Sheets

(51) Int. Cl.
*A61N 1/372* (2006.01)
*A61N 1/05* (2006.01)

(52) U.S. Cl.
CPC ..... *A61N 1/36139* (2013.01); *A61N 1/36157* (2013.01); *A61N 1/37205* (2013.01); *A61N 1/37211* (2013.01)

(56) References Cited

U.S. PATENT DOCUMENTS

| | | | |
|---|---|---|---|
| 7,636,602 | B2 | 12/2009 | Fassio et al. |
| 8,855,767 | B2 | 10/2014 | Faltys et al. |
| 2001/0031991 | A1 | 10/2001 | Russial |
| 2006/0009807 | A1* | 1/2006 | Ostroff ................ A61N 1/3912 607/5 |
| 2009/0157142 | A1 | 6/2009 | Cauller |
| 2013/0131761 | A1 | 5/2013 | Della Santina et al. |

OTHER PUBLICATIONS

Carmena, J., "Becoming Bionic", IEEE Spectrum, vol. 49, No. 3, pp. 25-29 (Mar. 2012).

Chen, et al., "A Fully Integrated 8-Channel Closed-Loop Neural-Prosthetic CMOS SoC for Real-Time Epileptic Seizure Control", IEEE Journal of Solid-State Circuits, vol. 49, No. 1, pp. 232-247 (Jan. 2014).

Cogan, S., "Neural Stimulation and Recording Electrodes", Annual Review of Biomedical Engineering, vol. 10, pp. 275-309 (Aug. 2008).

Constandinou, et al., "A Partial-Current-Steering Biphasic Stimulation Driver for Vestibular Prostheses", IEEE Transactions on Biomedical Circuits and Systems, vol. 2, No. 2, pp. 106-113 (Jun. 2008).

Farahmand, et al., "Programmable High-Output-Impedance, Large-Voltage Compliance, Microstimulator for Low-Voltage Biomedical Applications", Proceedings of the 34th Annual International Conference of the IEEE Engineering in Medicine and Biology Society (EMBC), pp. 863-866 (Aug.-Sep. 2012).

Karkare, et al., "A 130- W, 64-Channel Neural Spike-Sorting DSP Chip", IEEE Journal of Solid-State Circuits, vol. 46, No. 5, pp. 1214-1222, (May 2011).

Langlois, et al., "High-Power Integrated Stimulator Output Stages With Floating Discharge over a Wide Voltage Range for Nerve Stimulation", IEEE Transactions on Biomedical Circuits and Systems, vol. 4, No. 1, pp. 39-48, (Feb. 2010).

Lee, et al., "A 64 Channel Programmable Closed-Loop Neurostimulator with 8 Channel Neural Amplifier and Logarithmic ADC", IEEE Journal of Solid-State Circuits, vol. 45, No. 9, pp. 1935-1945 (Sep. 2010).

Lee, et al., "A Power-Efficient Switched-Capacitor Stimulating System for Electrical/Optical Deep-Brain Stimulation", 2014 IEEE International Solid-State Circuits Conference (ISSCC) Digest of Technical Papers, pp. 414-415 (Feb. 2014).

Lee, et al., "A Power-Efficient Wireless System With Adaptive Supply Control for Deep Brain Stimulation", IEEE Journal of Solid-State Circuits, vol. 48, No. 9, pp. 2203-2216 (Sep. 2013).

Monge, et al., "A Fully Intraocular High-Density Self-Calibrating Epiretinal Prosthesis", IEEE Transactions on Biomedical Circuits and Systems, vol. 7, No. 6, pp. 747-760 (Dec. 2013).

Moritz, et al., "Direct control of paralysed muscles by cortical neurons", Nature, vol. 456, No. 7222, pp. 639-642 (Dec. 2008).

Nadeau, et al., "A flexible high voltage biphasic current-controlled stimulator", IEEE Biomedical Circuits and Systems Conference (BioCAS 2006), pp. 206-209, (Nov.-Dec. 2006).

Noorsal, et al., "A Neural Stimulator Frontend With High-Voltage Compliance and Programmable Pulse Shape for Epiretinal Implants", IEEE Journal of Solid-State Circuits, vol. 47, No. 1, pp. 244-256 (Jan. 2012).

Pelliconi, et al., "Power Efficient Charge Pump in Deep Submicron Standard CMOS Technology", IEEE Journal of Solid-State Circuits, vol. 38, No. 6, pp. 1068-1071 (Jun. 2003).

Pepin, et al., "High-voltage compliant, capacitive-load invariant neural stimulation electronics compatible with standard bulk-CMOS integration", 2014 IEEE Biomedical Circuits and Systems Conference (BioCAS), pp. 1-4 (Oct. 2014).

Shulyzki, et al., "CMOS Current-Copying Neural Stimulator with OTA-Sharing", Proceedings of the 2010 IEEE International Symposium on Circuits and Systems, pp. 1232-1235 (May-Jun. 2010).

Sooksood, et al., "An Active Approach for Charge Balancing in Functional Electrical Stimulation", IEEE Transactions on Biomedical Circuits and Systems, vol. 4, No. 3, pp. 162-170 (Jun. 2010).

Stein, et al., "Reanimating limbs after injury or disease", Trends in Neurosciences, vol. 28, No. 10, pp. 518-524 (Oct. 2005).

Thurgood, et al., "A Wireless Integrated Circuit for 100-Channel Charge-Balanced Neural Stimulation", IEEE Transactions on Biomedical Circuits and Systems (BioCAS), vol. 3, No. 6, pp. 405-414 (Dec. 2009).

Van Dongen, et al., "A Power-Efficient Multichannel Neural Stimulator Using High-Frequency Pulsed Excitation from an Unfiltered Dynamic Supply", IEEE Transactions on Biomedical Circuits and Systems, vol. 10, No. 1, pp. 61-71, (Nov. 2014).

Ismail, et al., "A 12-V Charge Pump-Based Square Wave Driver in 65-nm CMOS Technology", IEEE Asian Solid-State Circuits Conference, vol. 15-2, pp. 237-240, Nov. 2014.

* cited by examiner

ANALOG FRONT-END CIRCUITRY FOR BIPHASIC STIMULUS SIGNAL DELIVERY FINDING USE IN NEURAL STIMULATION

CROSS-REFERENCE TO RELATED APPLICATION(S)

This application claims the benefit under 35 U.S.C. § 119 of the earlier filing date of U.S. Provisional Application Ser. No. 62/181,046 filed Jun. 17, 2015, the entire contents of which are hereby incorporated by reference in their entirety for any purpose.

STATEMENT REGARDING RESEARCH & DEVELOPMENT

This invention was made with government support under EEC-1028725 awarded by the National Science Foundation (NSF). The government has certain rights in the invention.

TECHNICAL FIELD

Embodiments of the invention relate generally to circuitry for neural stimulation. Examples of H-bridge circuits for provision of biphasic, constant-current signals are described.

BACKGROUND

Rapid advances in understanding brain function, neural connectivity and neural plasticity are providing opportunities to develop systems to aid the diagnosis and treatment of neurological disorders. Electrical neural stimulators are being used alongside neural recording systems to enable bidirectional interactions with the nervous system and realize new neuroprostheses and rehabilitation methods.

DETAILED DESCRIPTION

Figure 1:
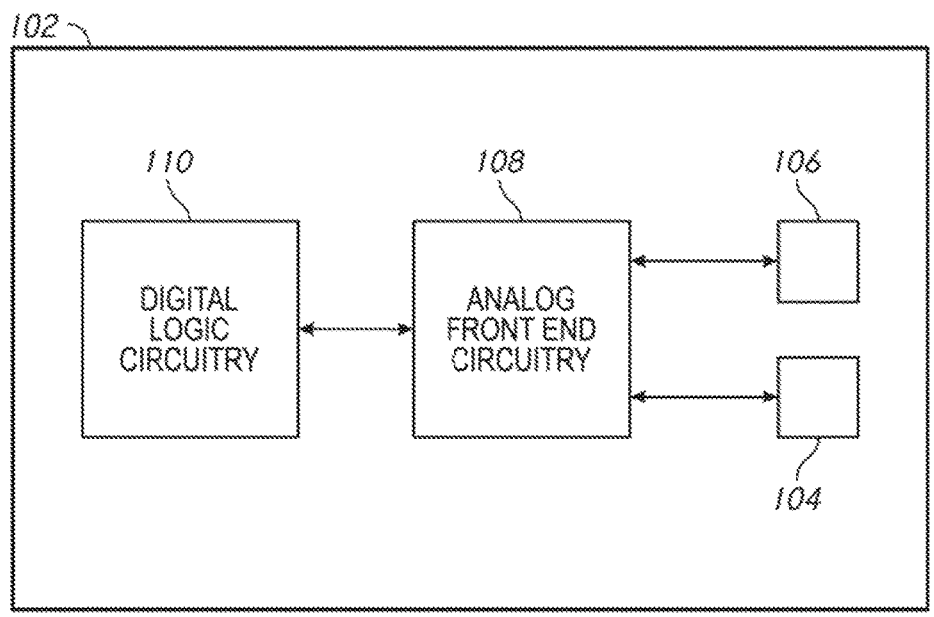
FIG. 1 is a schematic illustration of a chip for neural stimulation arranged in accordance with examples described herein.

Certain details are set forth below to provide a sufficient understanding of embodiments of the invention. However, it will be clear to one skilled in the art that embodiments of the invention may be practiced without various of these particular details. In some instances, well-known or well-understood circuits, circuit elements, control signals, timing protocols, fabrication techniques, and software operations have not been shown in detail in order to avoid unnecessarily obscuring the described embodiments of the invention.

To make bidirectional neural interfaces viable for medical technologies, the implanted electronics should be robust, low power, wireless (communication and power), and preferably in examples, as small a solution as possible (e.g. tiny). Many bidirectional neural interface applications (e.g. cortico-spinal prostheses, automated seizure suppression, closed-loop deep-brain stimulation) may require digital signal processing within the implant, as to control the stimulator in response to recorded neural activity, in real-time. To minimize the size and complexity of the implant, it may be desirable to integrate as many components as possible as closely as possible. For example, it may be advantageous to provide multiple components of a bidirectional neural interface integrated on a same chip (e.g. fabricated using a same semiconductor process flow). However, a barrier to implementing the neural interface electronics on a single bulk-CMOS chip may relate to the high voltages often required to evoke neural activity using electrical stimulation.

These large voltages are the result of driving charge-balanced, biphasic stimulus current through the electrode-tissue-interface impedance ($Z_E$). For this reason, existing bulk-CMOS neural stimulators may have limited voltage compliance (e.g. ±VDD/2), which may be constrained by the foundry-defined voltage-ratings of the implemented active devices (e.g. VDD=1V) in order to prevent gate-oxide breakdown and ensure reliable performance. Stimulators with voltage compliance beyond ±VDD/2 generally either still restrictively limit the overall stimulator compliance (e.g. <±VDD), have performance limitations in terms of driving stimulus through electrodes with varied frequency-dependent impedance characteristics, and/or place the front-end design burden on high-performance/specialized analog circuits (e.g. floating current-DACs) which may be difficult to implement across advanced CMOS technologies.

Examples described herein may be useful in implementing practical, electrical neural stimulation interfaces using modern silicon CMOS technologies. Generally, there may be a discrepancy between low-voltage limitations of modern CMOS devices (e.g. devices such as transistors that may support voltages across the devices of 1, 2, or 3 Volts in some examples) and the larger stimulation voltages often used and/or observed at response-evoking stimulus levels (e.g. voltages such as 5, 10, 11, or 12 Volts in some examples). Examples of analog front-end circuitry are described which may drive biphasic, constant-current signals through a wide range of electrode impedances while being safely implemented in a low-voltage, bulk-CMOS technology. In this manner, a biphasic, constant-current signal at a high voltage may be provided, while utilizing devices (e.g. transistors) which tolerate only lower voltages applied across them. This may allow for the fabrication of digital circuitry together with the analog front-end circuitry on a single chip. With bulk-CMOS compatibility, example analog front-end circuitry described herein may be integrated on the same silicon chip with other blocks used for example implantable bidirectional neural interfaces (e.g. high-density neural recording, DSP, memory, wireless interfaces, or combinations thereof). Providing the digital circuitry together with the analog front end on a single chip may generally reduce the size and complexity of required interconnections, which may reduce the size of an overall device or system required for neural stimulation and/or recording. Avoiding multiple chips may be beneficial because, for example, if multiple chips need to be connected, each generally must be "packaged" (which may increase the dimension of the system in both length, width, etc.), and then the chips would need to be connected on a common printed-circuit-board (PCB). Each chip would require some amount of space around it on the PCB for interconnections (further increasing the total system dimensions). Multiple chip systems tend to be more power hungry as well (e.g. each chip has its own power-wasting bias circuitry). Accordingly, consolidation of components of a bidirectional neural interface into a single chip (e.g. analog front-end and digital logic, memory, wireless interface, etc.) may be advantageous in some examples.

Moreover, analog front-end circuitry for neural stimulation systems may need to drive a charge-balanced current waveform between an "active" and "return" electrode, with the targeted neural tissue between said electrodes. The electrodes serve as electronic-to-ionic current transducers, and together, the two electrodes and the tissue (through which the stimulus is driven) present the electrode-tissue-interface impedance, $Z_E$. Depending on the electrodes used, $Z_E$ can be complex, as well as non-linear. Existing electrode-interfacing electronics often model $Z_E$ as a series R-C element, with R and C set to approximate the frequency response of a given electrode configuration. However, a more realistic $Z_E$ model includes a resistance in-parallel with the "C" of the said R-C model. Accordingly, a $Z_E$ may be modeled as, for example, $C_{DL} \| R_{CT} + R_S$ electrode-tissue-interface to more accurately model the frequency-dependent voltage observed across a given active-return electrode pair when applied current stimulus. In such an approximation, $C_{DL}$ may represent the "double-layer capacitance" transduction pathway; $R_{CT}$, the "charge-transfer" resistance, modeling the redox-driven transduction pathway; and $R_S$, the "spreading" or "solution" resistance, models the resistance to ionic current flow within the tissue.

Tissue impedance, $Z_E$, as indicated by the linear-circuit-element approximation, may not just exhibit a "high" impedance (e.g. making high, bipolar electrode driving voltages desirable), but may also exhibit varying frequency-dependence (e.g. $Z_E$ can display both resistive and capacitive characteristics); furthermore, $Z_E$ may change during in-vivo operation and after prolonged use. Accordingly, examples described herein may not only provide high (and bipolar) voltage compliance, but also performance that is invariant (or relatively invariant) to the frequency-dependent characteristics of $Z_E$ (e.g. within the purely or primarily resistive to purely or primarily capacitive, and any phasor representation of impedance between these two real and imaginary components).

Example topologies used in the front-end analog circuitry are based on a sink-regulated H-bridge. Stimulus current may be supplied using fully-integrated dynamic voltage supplies (DVSs), which may be controlled in closed-loop to have an output voltage approximately equal to the voltage of the electrode each supplies stimulus to. The stimulus waveform may be regulated by a single, low-voltage current-digital-to-analog converter (current-DAC), which can safely interface with the electrodes (which may be at high voltages) via high-voltage adapter (HVA) circuits.

To account for "capacitive-looking" electrodes and to provide unique, "electrode-invariant" performance, the example analog front-end circuitry described herein may utilize the balancing stimulus current to discharge the electrode-tissue interface impedance ($Z_E$). In some examples, only after full (or sufficient) $Z_E$ discharge has been detected is a DVS used to supply the remaining balancing stimulus.

Examples described herein may realize high-voltage, bulk-CMOS stimulator front-end circuitry which may provide: 1) voltage compliance decoupled from the VDD-rating of the implementing transistors; 2) the ability to drive charge-balanced, current-regulated stimulus through a wide range of $Z_E$, from resistive to capacitive (e.g. "electrode-invariant" performance); and 3) a design which is scalable across nm-scale CMOS technologies, leveraging the transistor as a switch as much as possible.

Examples described herein may provide analog and digital highly-integrated front-end circuitry for biphasic stimulus signal delivery which may find use in neural stimulation devices and systems.

Example analog front-end circuitry described herein may be used to drive constant-current biphasic stimulus, with voltage compliance decoupled from the VDD-rating of the implementing transistors; instead, the voltage compliance may only be restricted by the voltage limitations imposed by more voltage-tolerant structures like metal-to-metal capacitors, and/or, for example in a bulk-CMOS process, the reverse breakdown voltage of the p-substrate-to-deep-n-well junction.

FIG. 1 is a schematic illustration of a chip for neural stimulation arranged in accordance with examples described herein. The chip 102 includes digital logic circuitry 110, analog front-end circuitry 108, electrode 106, and electrode 104. The chip 102 may be implemented using a portion of a silicon substrate, although other substrates of other or additional materials may additionally or instead be used including, but not limited to, glass, oxide, polysilicon, polyimide, other polymers or flexible substrates, or combinations thereof. The digital logic circuitry 110 and analog front-end circuitry 108 may be integrated on the same chip 102. Integration on the same chip generally refers to the digital logic circuitry 110 and analog front-end circuitry 108 sharing at least a portion of a same substrate. For example, at least some devices used to implement the digital logic circuitry 110 and the analog front-end circuitry 108 may be fabricated on the same substrate. Fabrication on the same substrate may refer, for example, to the use of at least portions of a same process flow (e.g. a CMOS process flow). Fabrication in the same substrate may refer, for example, to portions of a same substrate being used to form portions of the transistors in the digital logic circuitry 110 and the analog front-end circuitry 108. The chip 102 may be a portion of a larger substrate, e.g. a wafer, sheet, or roll, on which multiple products may be fabricated and diced, cut, or otherwise divided into individual units, such as the chip 102.

The electrode 106 and electrode 104 may be externally-accessible electrodes. For example, they may have one or more conductive surfaces which are able to be electrically connected to other structures (e.g. electrodes for contacting biological tissue for neurostimulation, return electrodes for contacting biological tissue for neural stimulation, skull screws, or other neural stimulation or recording structures). In some examples, the electrode 104, electrode 106, or both, may themselves have a shape suitable for neural stimulation and/or recording (e.g. may have protrusions, needle-like shapes, screw-like shapes, or other features for stimulating and/or recording neural structures). The electrode 104, electrode 106, or both, may be implemented generally using any of a variety of conductive materials including, but not limited to metals such as aluminum, titanium, or copper. Generally, the analog front-end circuitry 108 may provide biphasic, constant-current stimulus signals to the electrode 106 and electrode 104.

The chip 102 may include additional externally-accessible pads (e.g. pins or I/O) or other electronic connectors. For example, pads may be included for power supply, reference, current source, clock, or other signals utilized by the analog front-end circuitry 108 and/or digital logic circuitry 110. In some examples, pads may be provided for input and/or output to and/or from the chip 102, such as pads for data input and/or output which may be compatible with electronic communication standards such as, but not limited to, USB or HDMI. Pads may be externally connected to an electrode, e.g. for interfacing with biological tissue, fluid, and/or ions.

The digital logic circuitry 110 may be fabricated on the substrate of the chip 102. The digital logic circuitry may include any of a variety of circuit elements including transistors, capacitors, inductors, and/or resistors. Elements, such as transistors, used to implement the digital logic circuitry 110 may generally be designed for operation with a particular power supply voltage, and/or for a plurality of power supply voltages. The particular power supply voltage or voltages may be a low power supply voltage in examples described herein, such as but not limited to, less than 0.8 V in some examples, less than 0.9 V in some examples, less than 1.0 V in some examples, less than 1.1 V in some examples, less than 1.2 V in some examples, less than 1.3 V in some examples, less than 1.4 V in some examples, less than 1.5 V in some examples, less than 1.6 V in some examples, less than 1.7 V in some examples, less than 1.8 V in some examples, less than 1.9 V in some examples, less than 2.0 V in some examples, less than 2.1 V in some examples, less than 2.2 V in some examples, less than 2.3 V in some examples, less than 2.4 V in some examples, less than 2.5 V in some examples, less than 2.6 V in some examples, less than 2.7 V in some examples, less than 2.8 V in some examples, less than 2.9 V in some examples, less than 3.0 V in some examples, less than 3.1 V in some examples, less than 3.2 V in some examples, less than 3.3 V in some examples, less than 3.4 V in some examples, less than 3.5 V in some examples. Common transistor fabrication processes may provide transistors rated for a 1V power supply, 2.5V power supply, or 3.3V power supply, for example. The power supply voltage may be referred to as $V_{DD}$ herein (e.g. a voltage at a drain of a transistor). The transistors in the digital logic circuitry 110 may, for example, have deleterious effects (e.g. oxide breakdown) when using power supplies greater than the designed power supply voltage. It is this designed power supply voltage which may limit the voltage output range of existing neural stimulation analog front-end circuitry fabricated in a same process as the digital logic circuitry 110.

Instead of or in addition to digital logic circuitry 110, the chip 102 may include other blocks for implantable neural interface implementation including, but not limited to, biasing blocks, power regulation blocks, neural recording circuitry, analog/mixed-signal neural networks, a digital signal processor, memory, wireless interface circuitry, wireless, power circuitry, energy harvesting circuitry, or combinations thereof. The digital logic circuitry 110 and/or other blocks for implantable neural interface implementation may include CMOS electronics (e.g. digital, analog, and/or mixed signal) for which the power voltage level used by the electronics (e.g. Vdd) is at or below device ratings.

The analog front-end circuitry 108 may also be fabricated on the substrate of the chip 102. The analog front-end circuitry 108 may include any of a variety of circuit elements including transistors, capacitors, inductors, and/or resistors. Circuit elements of the analog front-end circuitry 108 may also be designed for operation with the same particular power supply voltage as the digital logic circuitry 110. However, the analog front-end circuitry 108 may provide a biphasic stimulus signal having a voltage amplitude greater than the power supply voltage used to implement the circuit components. In some examples, the biphasic stimulus signal has a voltage amplitude greater than two times the power supply voltage. In some examples, the biphasic stimulus signal has a voltage amplitude greater than three times the power supply voltage. In some examples, the biphasic stimulus signal has a voltage amplitude greater than four times the power supply voltage. In some examples, the biphasic stimulus signal has a voltage amplitude greater than five times the power supply voltage. In some examples, the biphasic stimulus signal has a voltage amplitude greater than six times the power supply voltage. In some examples, the biphasic stimulus signal has a voltage amplitude greater than seven times the power supply voltage. In some examples, the biphasic stimulus signal has a voltage amplitude greater than eight times the power supply voltage. In some examples, the biphasic stimulus signal has a voltage amplitude greater than nine times the power supply voltage. In some examples, the biphasic stimulus signal has a voltage amplitude greater than or equal to ten times the first power supply voltage. In some examples, the biphasic stimulus signal has a voltage amplitude greater than or equal to twenty times the first power supply voltage. In some examples, the biphasic stimulus signal has a voltage amplitude greater than or equal to thirty times the first power supply voltage. For example, in some examples described herein, transistors used to implement the analog front-end circuitry 108 may be designed for operation with power supplies of 1V and 2.5V, while the biphasic stimulus signal may have a voltage amplitude of 10V or greater in some examples, 20V or greater in some examples, 30V or greater in some examples. Generally, any output voltage may be achieved which may be subject to the chip technology involved (e.g. for bulk CMOS, a limit may be the reverse breakdown voltage which may vary from process to process).

The analog front-end circuitry 108 may provide the biphasic stimulus signal between the electrode 106 and the electrode 104. The biphasic stimulus signal may generally be implemented using a signal having two phases—a first phase having a voltage and current amplitude of one polarity, and a second phase having a voltage and/or current amplitude of an opposite polarity. The biphasic stimulus signal may be a constant-current signal providing a constant current amount in a first direction followed by a constant current amount in a second direction. In some examples, the current of the leading phase is negative (e.g. is being sourced into the return electrode), which may serve to depolarize neurons near the active electrode, while the current of the next phase, which may be referred to as the balancing phase, is positive (e.g. is being sourced into the active electrode), and of equal amplitude and duration as the leading phase, as to make the stimulus charge-balanced. The biphasic stimulus signal may have a pulse-width (e.g. the duration of each phase of a biphasic pulse), a pulse amplitude, and a pulse frequency (e.g. a rate at which biphasic pulses are delivered). Depending on the stimulation application and electrodes used, the stimulus parameters may vary significantly. However, generally, stimulus amplitudes may fall between 10 μA and 10 mA, pulse-widths between 10 μs and 1 ms, and pulse frequencies below 300 Hz, although other parameters may be used in other examples. The constant-current amplitude of the first phase may not match the second phase in some example biphasic pulses. Generally, values for the parameters may be chosen such that total charge delivered in a biphasic pulse may be around 0.

The analog front-end circuitry 108 may be implemented using a sink-regulated H-bridge. In some examples, the chip 102 may further include a controller configured to cycle the H-bridge (and/or dynamic voltage supplies used to provide voltages for the biphasic stimulus signal) through a plurality of states to provide the biphasic stimulus signal.

The digital logic circuitry 110 and the analog front-end circuitry 108 may be in electronic communication with one another such that the digital logic circuitry 110 may, for example provide stimulus signals for use by the analog front-end circuitry 108. The analog front-end circuitry 108 may provide neural recordings for storage and/or processing by the digital logic circuitry 110. The digital logic circuitry 110 may be used to communicate with other electronic devices not shown in FIG. 1 through off-chip wired and/or wireless interfaces, including, but not limited to, Wi-Fi, Bluetooth, or combinations thereof.

Figure 2:
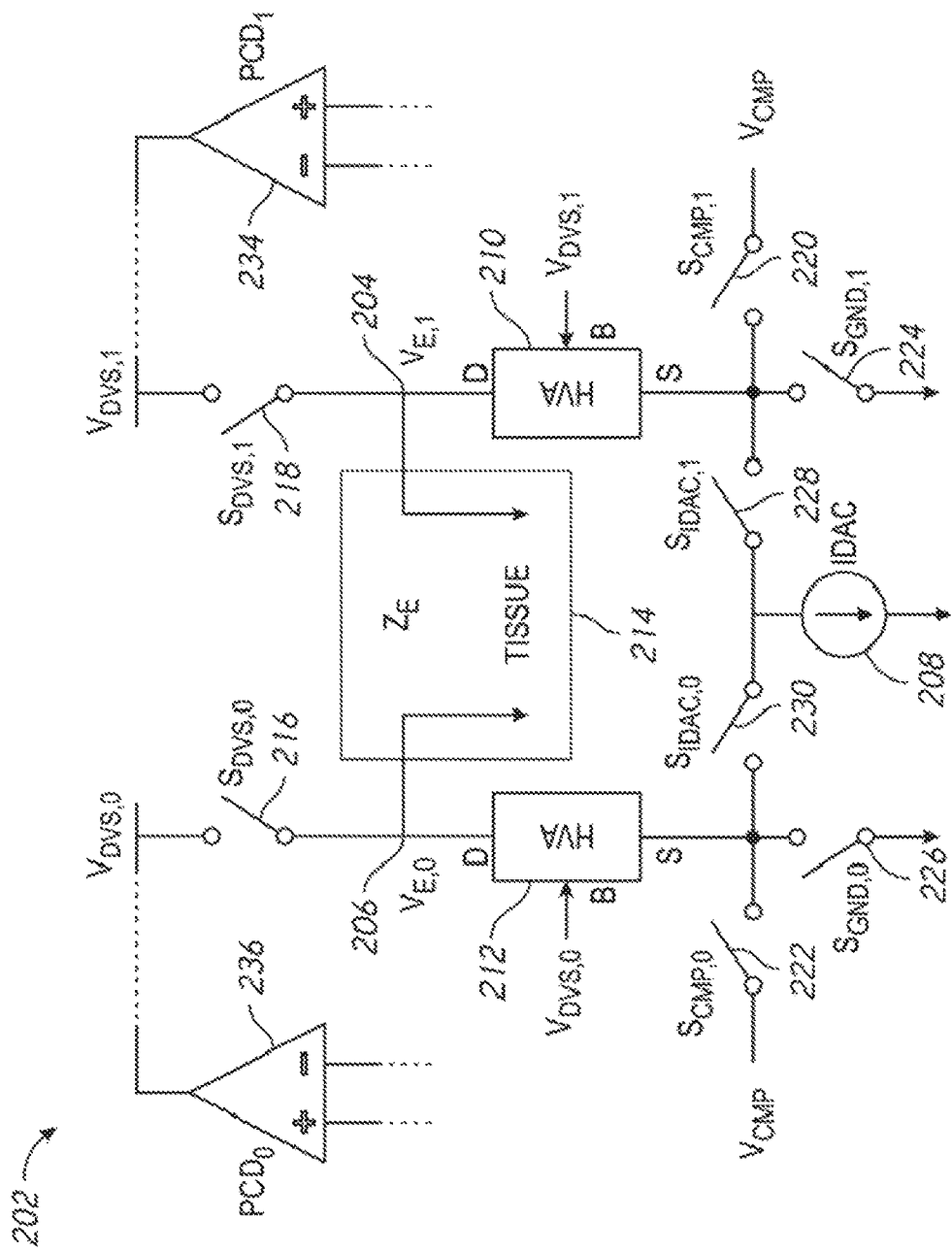
FIG. 2 is a schematic illustration of analog front-end circuitry having an H-bridge topology arranged in accordance with examples described herein.

FIG. 2 is a schematic illustration of analog front-end circuitry having an H-bridge topology arranged in accordance with examples described herein. The analog front-end circuitry 202 includes node 204 and node 206, high voltage adapter circuitry (HVA), including HVA 210 and HVA 212, a current digital-to-analog converter (current DAC 208), current driver circuitry 234, current driver circuitry 236, and switches including switch 216, switch 218, switch 220, switch 222, switch 224, switch 226, switch 228, and switch 230. The analog front-end circuitry 202 may be used to implement the analog front-end circuitry 108 of FIG. 1, for example.

One side of the H-bridge topology of FIG. 2, the node 204 is connected to switch 218, which may couple and/or decouple the node 204 to the current driver circuitry 234. The node 204 is also connected to HVA 210. The HVA 210 is connected to three switches, switch 220, switch 224, and switch 228. Switch 220 may couple and/or decouple the HVA 210 from a voltage comparator (not shown in FIG. 2 but indicated by $V_{CMP}$). The switch 224 may couple and/or decouple the HVA 210 from a reference voltage (ground in the example shown in FIG. 2). The switch 228 may couple and/or decouple the HVA 210 from the current DAC 208.

On another side of the H-bridge topology of FIG. 2, the node 206 is connected to switch 216, which may couple and/or decouple the node 206 to the current driver circuitry 236. The node 206 is also connected to HVA 212. The HVA 212 is connected to three switches, switch 222, switch 226, and switch 230. Switch 222 may couple and/or decouple the HVA 212 from a voltage comparator (not shown in FIG. 2 but indicated by $V_{CMP}$). The switch 226 may couple and/or decouple the HVA 212 from a reference voltage (ground in the example shown in FIG. 2). The switch 230 may couple and/or decouple the HVA 210 from the current DAC 208.

While the analog front-end circuitry 202 of FIG. 2 is shown with two sides (e.g. legs) of an H-bridge circuitry, other numbers of legs may be used in other examples, for example where more than one stimulus electrode may be used with a shared return electrode. Each side may include respective current driver circuitry, node, HVA, and switches similar to those shown in FIG. 2. For example, current DAC 208 may be shared amongst additional circuit legs, such that the "H-bridge" topology (which may not actually then be an 'H' in shape), may have 2, 3, 4, 5, 6, 7, 8, 9, 10, or other numbers of legs in some examples to provide for a stimulus signal delivered between 2, 3, 4, 5, 6, 7, 8, 9, 10, or other numbers of electrodes.

The node 204 and the node 206 may be implemented using electrodes and/or electrically connected to electrodes for neural stimulation of tissue 214. One electrode may be referred to as a stimulus (e.g. active) electrode and another as a return electrode. Generally any type of tissue may be stimulated in accordance with examples described herein, including, but not limited to, brain, spine, nerve, muscle, organ, or combinations thereof. The node 204 and the node 206 may be used, for example, to implement (and/or may be implemented by) the electrode 104 and electrode 106 of FIG. 1.

The current driver circuitry 234 and current driver circuitry 236 are shown using an op-amp symbol, and in some examples may be implemented using op-amps, however the op-amp symbol in FIG. 2 is intended to be merely representative of the feedback functionality of the current driver circuitry 234 and current driver circuitry 236. The current driver circuitry 234 and current driver circuitry 236 are each configured to provide high voltages (e.g. stimulus voltages). The high voltage produced by current driver circuitry 234 and current driver circuitry 236 may be the high voltage of a biphasic stimulus signal described herein, for example with return to FIG. 1. In some examples, the current driver circuitry 234 and current driver circuitry 236 include respective switched-capacitor power supplies for provision of the high voltage ($V_{DVS,1}$ and $V_{DVS,0}$ as shown in FIG. 2). The high voltage may be a voltage that is larger (e.g. twice as large or greater, three times as larger or greater, or ten times as large or greater) than a power supply used to supply transistors of the analog front-end circuitry 202, for example, as described with reference to FIG. 1.

The current driver circuitry 234 and current driver circuitry 236 may each include a dynamic voltage supply (DVS, e.g. a switched-capacitor power supply) and may generally operate in two modes, 1) a first mode to supply stimulus current while dynamically generating a 0-to-VMAX voltage that may be sufficient to keep the current DAC 208 from dropping-out (e.g. keeps current DAC 208 devices in saturation) and 2) a second mode to subsequently track a discharging electrode voltage back down to low voltages, as to keep the attached HVA 210 or HVA 212 properly biased and the switch to the electrode (e.g. a diode) off. Accordingly, the current driver circuitry 234 and current driver circuitry 236 may each include a controller, which may be a clocked controller, used to cycle the analog front-end circuitry 202 through various states described herein.

The HVA 210 and HVA 212 are coupled to node 204 and node 206 respectively. The HVA 210 and HVA 212 may protect the current DAC 208, which may operate on lower voltages than provided by the stimulus signal, from the node 204 and node 206 which may be placed at a higher voltage than suitable for the current DAC 208 by the stimulus signal. The HVA 210 and HVA 212 may effectively be considered to function as conducting, high-voltage-tolerant NMOS devices (e.g. with gates biased to a low-voltage), and accordingly protect the "low-side" circuits (e.g. switches and current-DAC) from potentially high electrode voltages while allowing these same circuits to interface with the electrodes. Each HVA may be provided with a bias voltage, and the input impedance of the HVA bias may be high as seen by the source of the bias (e.g. the dynamic voltage supply on a same side of the H-bridge topology). High impedance of the HVA bias generally refers to the impedance being purely or nearly purely capacitive. To aid in proper HVA function, the bias voltage may be approximately equal to the voltage of the electrode the HVA interfaces with.

Accordingly, each HVA may be provided this bias input from the DVS on the same side of the H-bridge, which may be kept at the same voltage (approximately) as the electrode throughout stimulus delivery via current driver operation.

The current DAC 208 may be implemented using any suitable current source, and may be implemented in a bulk CMOS process. As shown, the current DAC 208 is arranged in a sink configuration such that the analog front-end circuitry 202 provides a current-sink topology where current is sunk through the two sides of the H-bridge by the current DAC 208.

All or some of the switches shown in FIG. 2, including switch 216, switch 218, switch 220, switch 222, switch 224, switch 226, switch 228, and switch 230 may be implemented using diodes, transistors, fuses, or combinations thereof. The switches may be controlled by the current driver circuitry 234 and current driver circuitry 236 to provide for delivery of a biphasic voltage signal, in some examples with a constant-current (e.g. a stimulus signal). The stimulus signal may in some examples be delivered in a manner which is invariant (or has improved invariance) to the capacitive and/or resistive behavior of the tissue 214.

Each node 206 and node 204 via an HVA, may be connected to the current DAC 208, reference voltage (e.g. ground), or to a shared comparator (CMP) by properly configuring the corresponding switches (e.g. Switch 220, switch 224 and switch 228 in the case of the node 204 and switch 222, switch 226 and switch 230 in the case of node 206). Those six switches may be referred to as "low-side" switches. Each side has a dedicated low-side switch set, including the three mentioned switches. The shared comparator may be used during stimulus delivery (e.g. during the discharge of $Z_E$ via the stimulus current) to detect when the current DAC 208 voltage falls under the current DAC dropout voltage where the transistors have a high output resistance, and high current accuracy region of the current source; e.g. $V_{dsat}$, ($V_{GS}-V_T$), or $V_{OV}$, depending on the nomenclature, and assuming a MOS device, while $V_{CE(SAT)}$ for a Bipolar device. Like the current DAC 208, no special voltage precautions need to be taken in implementing these switches, or the comparator, since all interface with the voltage-protected, low-side of an HVA.

The "high-side" switches (e.g. Switch 216 and switch 218) directly interface with the nodes node 206 and node 204, which may be at high voltages, and therefore the implementation of these switches may be more complex.

However, when a given node is at a high-voltage, a current driver circuit will generally be forcing the corresponding supply voltage to an approximately equal level, resulting in a low-voltage (e.g. ≤VDD) across the associated high-side switch; this can give the designer flexibility in the way the high-side switches are implemented. However, in some examples, for simplicity and robustness, diodes (e.g. with the n-terminal connected to the electrode) may be used to implement switch 216 and switch 218, with ON/OFF functionality provided by the current driver controlled operation of the high voltage power supplies.

Accordingly, examples of analog front-end circuitry described herein may require the use of only two specialized circuits (e.g. DVSs and HVAs), with other functionality provided by circuits that can be implemented using standard, low-voltage topologies. The DVS may be implemented as a switched based structure and the HVA may be implemented using a fairly passive circuit that mainly relies on the operation of the DVS in feedback to protect the low-side circuits from potentially high electrode voltages. Considering the implementation of these "specialized" blocks and that the remainder of the front-end is made up of switches, digital circuits can be used to directly control most, if not all, of the driver. Accordingly, a state-machine can be used to guide the front-end circuitry through the various states to result in biphasic, constant-current stimulation.

Generally, the front-end circuitry described herein may be controlled (e.g. progressed through states) by a digital finite state machine. Each front-end state may have an associated current driver circuitry (active), current driver circuitry (return), HVA(active), and HVA(return) configuration, as well as an associated configuration of the set of low-voltage switches which sits under an HVA (e.g. 2 identical sets, one for each side of h-bridge): each current driver circuitry may be provided with bus (e.g. a three-bit bus), the decoded value of which may set its configuration (e.g. TRACK, SUPPLY, RESET, OFF); each HVA may be provided with a bus (e.g. a 2 bit bus), the decoded value of value of which sets its configuration; and each switch may be provided with a bus (e.g. a 3 bit bus), the decoded value of which sets its configuration (e.g. connected to ground, connected to IDAC, connected to comparator, etc.).

In some examples, the outputs of a front-end controlling digital state-machine are provided on these digital busses, and the state-machine may be implemented be on-chip. However, in some examples, state-machine timing may be controlled off-chip with a micro controller, and a bus (e.g. a 4 bit bus encoding the front-end state) may be provided to the chip as input. For example, the bus provided to the chip as input may carry the bits which are the "select" inputs to an on-chip multiplexer structure, which may select the set of bus values (which in some examples may be previously loaded onto the chip with serial I/O scan chain, for all states, for example) to forward to the front-end blocks (e.g. current driver circuitry, HVAs, switch-sets).

Figure 3:
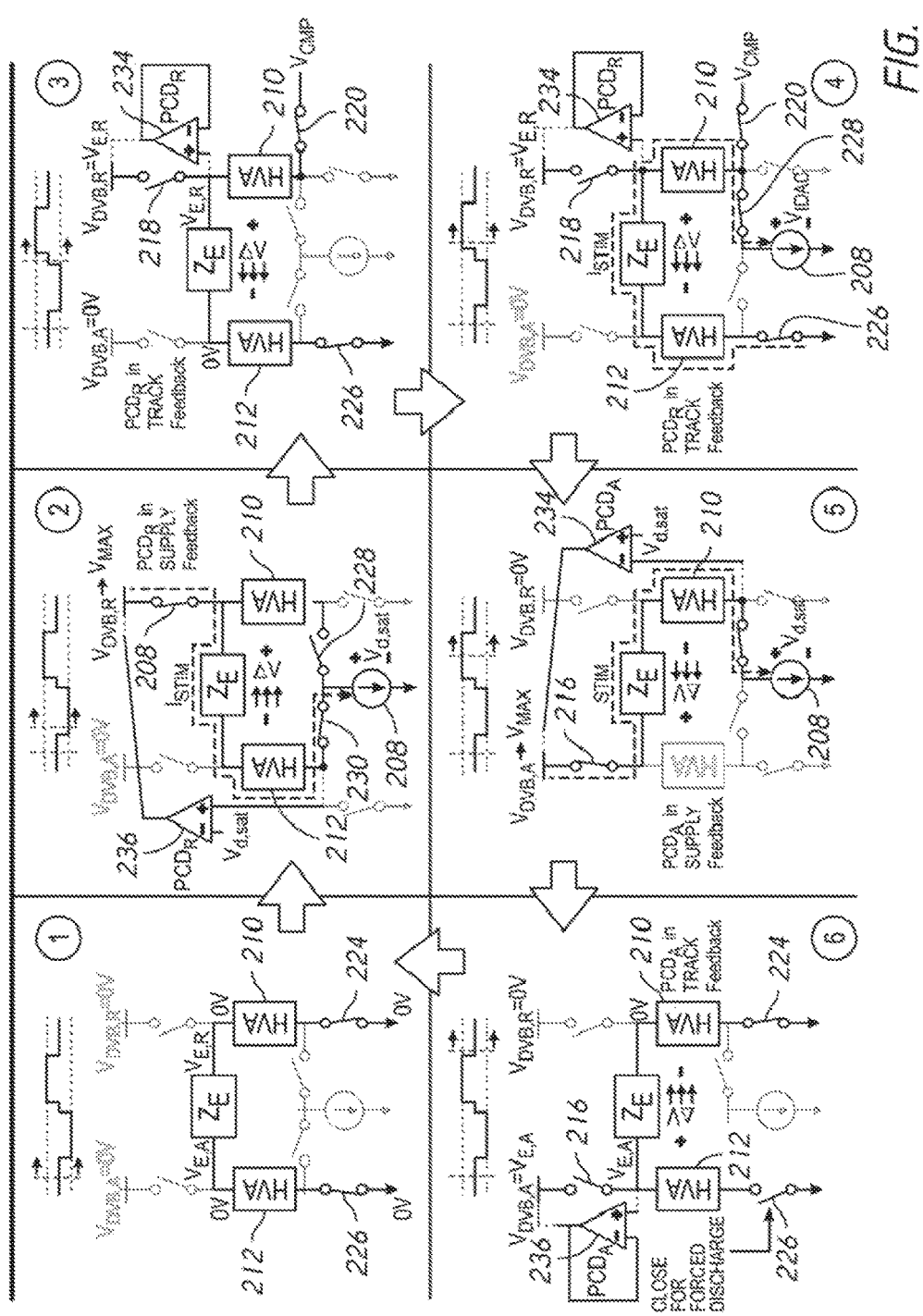
FIG. 3 is a schematic illustration of the analog front-end circuitry 202 of FIG. 2 in various operational states.

FIG. 3 is a schematic illustration of the analog front-end circuitry 202 of FIG. 2 in various operational states. Same reference numbers are used for the circuit components and generally only the connected circuit components are shown in each state. Disconnected circuit components are minimized and/or not shown to assist in clarity. The states are numbered 1 through 6, and a depiction of the biphasic stimulus signal is shown in each state to aid in understanding which portion of the biphasic stimulus signal is delivered in each state. Generally, the current driver circuitry 236 and current driver circuitry 234 may control the analog front-end circuitry 202 to move through the phases shown in FIG. 3.

In the sequence of states, to account for "capacitive-looking" electrodes (e.g. capacitive behavior of tissue 214), the analog front-end circuitry 202 may use the balancing stimulus to discharge $Z_E$, which may hold a high voltage after the leading stimulus pulse is delivered (e.g. State 4 in FIG. 3). In some example, only after a low voltage comparator (CMP) detects $Z_E$ to be discharged is a dynamic voltage supply (e.g. a high voltage DVS) used to deliver the remaining balancing stimulus current.

With reference to FIG. 2 and FIG. 3 the "active" electrode will be referred to as the node or electrode that sees negative stimulus current (positive current being drawn out of the electrode) during the leading pulse, and positive stimulus current (positive current being sourced into the electrode) during the balancing pulse, while the "return" electrode sees the opposite current polarity. Because some example front-end circuitry described herein is symmetrical across $Z_E$ and mostly digitally controlled, the nodes can be configured (and reconfigured on-the-fly) as active/return or return/active.

For purposes of discussion, the node 206 will be designated as the active electrode (and node 204 as the return).

Accordingly, FIG. 3 illustrates how the FIG. 2 analog front-end circuitry 202 is guided through a specific sequence of "states" (with each state having a different front-end configuration) to drive biphasic, constant-current stimulus through tissue 214.

In a first state (labeled '1' in FIG. 3), the analog front-end circuitry 202 may be in an 'idle' state. The dynamic voltage supplies of the current driver circuitry 234 and the current driver circuitry 236 may be inactive and have fully discharged outputs, while the node 206 and node 204 are shorted to a reference voltage (e.g. chip ground, 0V). Accordingly, the reference voltage may be provided at both the node 206 and the node 204 by connecting the HVA 210 and the HVA 212 to the reference voltage (e.g. by closing switch 226 and switch 224) and disconnecting the node 204 and node 206 from the high voltages (e.g. by opening and/or turning off switch 216 and switch 218). Since neither DVS is being actively controlled, the power consumption associated with this state may be low. Furthermore, since both DVSs are discharged to 0V (e.g. the same voltage as the electrodes) there may be little DC leakage into the tissue. In an alternative configuration, just one electrode may be shorted to the reference voltage, e.g. 0V, (for example, the node 204), while the other electrode see high-impedance (high-Z); in this alternative configuration the DVSs may still remain discharged and inactive.

In a second state (labeled '2' in FIG. 3), the analog front-end circuitry 202 may be in a state providing a negative stimulus. The current driver circuitry 236 may be coupled to the node 204 to provide a high voltage (e.g. $V_{MAX}$) to the node 204. Accordingly, the switch 218 may be closed and/or on. The HVA 212 may be connected to the current DAC 208 (e.g. by closing and/or turning off the switch 230). The HVA 210 may be disconnected from the current DAC 208 and the reference voltage (e.g. by opening the switches switch 228 and switch 224).

In this manner, the current DAC 208 is connected to the active-side of the H-bridge, the dynamic voltage supply of the current driver circuitry 236 is connected to the return electrode (e.g. Node 204), and the current driver circuitry 236 may be activated in its supply configuration (modeled by the op-amp shown in FIG. 2 and FIG. 3). As a result, negative $I_{STIM}$ current is seen by the active electrode (e.g. Node 206) while the return DVS sets the return electrode voltage (e.g. Node 204), as needed, to keep the current DAC 208 voltage above the IDAC dropout voltage, e.g. above the transistor $V_{dsat}$ (e.g. as to maximize the stimulator compliance); assuming a low-headroom IDAC design is used, $V_{dsat}$ may be no higher than a few hundred millivolts.

In a third state (labeled '3' in FIG. 3), the analog front-end circuitry 202 may be in an interphase delay state. This state may have a short duration, and begins after delivery of the leading pulse of the biphasic stimulus signal. The node 204 is disconnected from the current driver circuitry 236 (e.g. by closing or turning off switch 218). The HVA 212 is connected to the reference voltage (e.g. by closing or turning off switch 226). The HVA 210 is connected to the voltage comparator (e.g. using closing or turning off the switch 220).

Except for the switch 220, which connects the low-side of the return HVA 210 to the high-impedance, negative input of the comparator, all switches on the return-side of the H-bridge may be open or turned off. Accordingly, looking into the return-side of the H-bridge, the return electrode sees high-impedance. To keep $Z_E$ from floating, the active electrode (via the active HVA 212) may be connected to ground (e.g. through the switch 226).

If $Z_E$ exhibits capacitive characteristics, a significant fraction of the voltage developed across $Z_E$ by the end of the previous state (which may be significantly higher than VDD) may be maintained across $Z_E$ during this state. Additionally, the voltage applied to the active electrode at the State 2 to State 3 transition will result in a negative voltage shift at the return electrode, and the return electrode voltage may decrease during the interphase delay due to $Z_E$ self-discharge.

Accordingly, the return current driver circuitry 236 is placed in its track configuration (e.g. modeled by op-amp in FIG. 3), forcing the return DVS to track a potentially falling $V_{E,R}$ (e.g. $dV_{E,R}/dt \leq 0$).

This action primarily keeps the return HVA 210 properly biased (e.g. keeps $V_{DVS,R} \approx V_{E,R}$), but also keeps the voltage across switch 218 approximately zero, which may be advantageous, in terms of device reliability, in some examples, depending on the implementation of said switch.

The voltage comparator is connected during this state to allow its input capacitance to equalize with the voltage at the low-side of the HVA 210, so that, if needed, the dropout of the current DAC 208 can be detected right as State 4 begins (e.g. if $Z_E$ is mostly resistive). Accordingly, the comparator is being "primed" for a decision to-be-made in the next state, while being effectively disabled, with the comparator output ignored by an inactive dropout detection block.

In a fourth state, the analog front-end circuitry 202 is in a positive stimulus through impedance (e.g. $Z_E$) discharge state. The HVA 212 may be connected to the reference voltage (e.g. by closing or turning off the switch 226). The HVA 210 may be connected to the current DAC 208 and the voltage comparator (e.g. by closing and/or turning off switch 224 and switch 220).

Generally, the same configuration utilized in the previous state (the third state) may be maintained, except the node 204, via the HVA 210, is connected to the current DAC 208 (in addition to being connected to the dropout detecting voltage comparator).

As the current DAC 208 discharges $Z_E$ via sinking $I_{STIM}$, the return electrode voltage falls (as the return DVS tracks it) and the active electrode (e.g. Node 206) sees positive $I_{STIM}$. Accordingly, at some point during this state the return electrode voltage, and therefore the current DAC 208 voltage, will approach the $V_{d,sat}$ of the current DAC 208. But at the point of dropout, the 0 to 1 transition at the output of the comparator triggers the active dropout detector, which forces the front-end to transition to the configuration of the next state.

In a fifth state, the analog front-end circuitry 202 is in a positive stimulus through active current driver circuitry state. The current driver circuitry 234 may be connected to the node 206 (e.g. by closing or turning off the switch 216) to provide the high voltage to the node 206. The HVA 210 may be connected to the current DAC 208 (e.g. by closing and/or turning off the switch 228). The HVA 212 may be disconnected from the current DAC 208 and the reference voltage (e.g. by opening and/or turning off the switch 226 and switch 230).

The remainder of the balancing biphasic stimulus pulse is delivered by disconnecting the reference voltage (e.g. ground) from the node 206, connecting the DVS of the current driver circuitry 234 (initially at 0V) to the node 206, and placing the current driver circuitry 234 in its supply configuration. Accordingly, complementary to the State 2 front-end configuration, the current DAC 208 regulates positive $I_{STIM}$ through the node 206 while the active DVS supplies the stimulus current and has its voltage increased to keep the current DAC 208 voltage at $V_{d,sat}$.

In a sixth state, the analog front-end circuitry 202 is in a $Z_E$ discharge state. The node 206 may be disconnected from the current driver circuitry 234 (e.g. by opening and/or turning off the switch 216). The HVA 210 may be connected to the reference voltage (e.g. by closing and/or turning on the switch 224).

Due to a non-linear $Z_E$ and/or $Z_E$ having both capacitive and faradaic transduction mechanisms, a non-zero voltage may exist across $Z_E$ after well-balanced biphasic stimulus has been successfully delivered. This residual charge can either be allowed to passively discharge using the configuration shown in sixth state, or, with a slightly modified configuration, be forced to discharge by connecting the node 206 (via the HVA) to ground. In either case the active PCD (e.g. Current driver circuitry 236) is placed in its track configuration, to force its DVS to track the node 206 back down to 0V. Once $Z_E$ is fully discharged, the driver can be returned to the State 1 (e.g. Idle) configuration.

If a charge-balanced waveform has already been delivered and no blocking capacitors are used, then "passive discharge" may be employed to assure charge balance is maintained (e.g. without the application of auxiliary charge-balancing circuitry). However, if a blocking capacitor does exist in the stimulus path, then the "forced discharge" method can be readily employed, and the time-constant/magnitude of the discharge current can be modified, if desired, by adjusting the resistance of the switch connecting the active electrode to ground.

The transitions between the states shown in FIG. 3, including the control of any or all described switches, may be performed by the current driver circuitry described herein, which may include controllers configured to control the progression of states shown in FIG. 3.

Figure 4:
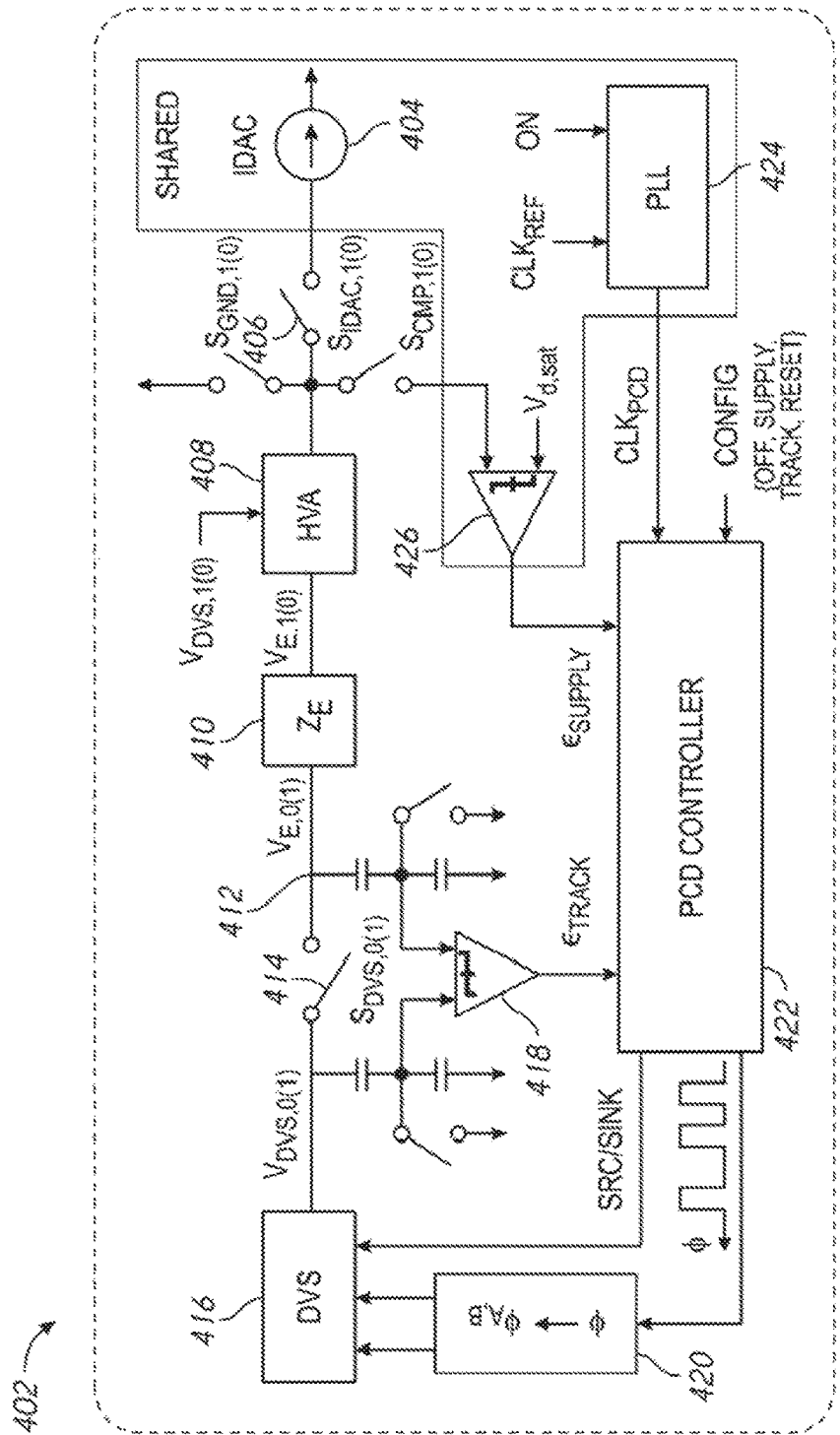
FIG. 4 is a schematic illustration of current driver circuitry arranged in accordance with examples described herein.

FIG. 4 is a schematic illustration of current driver circuitry arranged in accordance with examples described herein. The current driver circuitry 402 as shown includes current DAC 404, switches 406, HVA 408, impedance 410, node 412, switch 414, DVS 416, comparator 418, transform 420, controller 422, PLL 424, and comparator 426. All or portions of the current driver circuitry 402 may be used to implement the current driver circuitry 234 and/or the current driver circuitry 236 of FIG. 2 and FIG. 3. For ease of description, FIG. 4 illustrates components of the current driver circuitry 402 which overlap with components of the analog front-end circuitry 202 shown in FIG. 2. For example, the current DAC 404 may correspond with current DAC 208 of FIG. 2. The switches 406 may correspond with the switch 220, switch 224, and switch 228 of FIG. 2 (or the switch 222, switch 226, and switch 230). The HVA 408 may correspond with the HVA 210 or HVA 212 of FIG. 2. The impedance 410 may correspond with the tissue 214 of FIG. 2. The node 412 may correspond with the node 206 or node 204 of FIG. 2. The switch 414 may correspond with the switch 218 or switch 216 of FIG. 2. Accordingly, the depiction of the current driver circuitry 402 includes portions of the analog front-end circuitry 202 for ease of description.

In delivering biphasic constant-current stimulus, the proposed H-bridge front-end utilizes the coordinated operation of two current driver circuitry instantiations (e.g. positive-current driver (PCD) sub-systems), each controlling the output voltage of a dedicated dynamic voltage supply (DVS). The "PCI" nomenclature may be used in part because a function of the sub-system is to drive positive stimulus current into its associated electrode. Additionally, another or alternate function of a PCD may be to force its associated DVS to track the falling voltage of the same electrode, when no stimulus is supplied, so that all nodes within the PCD can be safely returned to low voltages.

The DVS 416 may be used to supply stimulus current across a voltage range of 0V to $V_{MAX}$. When unloaded (e.g. when the switch 414 at the DVS output is open) the DVS may be used to track the potentially falling voltage of the electrode that lies on the same side of the H-bridge.

Internally, the DVS 416 may be implemented using a switched-capacitor topology and operation, and variable voltage may be achieved at its output by being able to source and sink switched-capacitor current to an output capacitor. The SOURCE/SINK control bit shown as an input to DVS 416 may set the direction in which switched-capacitor current flows through the DVS 416, and the drive strength of the DVS 416 may be set by the frequency of the input pulse signal, $\Phi$, which may be transformed to complementary pulse signals $\Phi A$ and $\Phi B$ by the transform 420 before being used to directly drive the DVS 416. As the frequency of $\Phi$ is increased (within a range the DVS 416 is designed for), quanta of charge may move through the DVS 416 at a higher rate, resulting in higher switched-capacitor current. When loaded by a constant-current and placed in its SOURCE setting, the DVS 416 may be modeled as having a linear relationship (with negative slope) between output voltage (average output voltage) and the period (e.g. average period) of $\Phi$. When unloaded and in the SINK setting, the output of the DVS 416 can be discharged in a controlled fashion (e.g. to as low as 0V), with each pulse of $\Phi$ producing a small $-\Delta V$ at the DVS output.

When current driver circuitry 402 is activated, closed-loop feedback may be utilized to set the output voltage of the DVS 416; the error signal used to close the loop may be generated by one of the comparators shown in FIG. 4. The $\varepsilon$SUPPLY generating comparator 426 may be used to compare the detected current DAC 404 voltage to the desired current DAC 404 voltage (e.g. $V_{dsat}$, the IDAC dropout voltage). This comparator 426 may be shared by multiple instantiations of current driver circuitry (e.g. both current driver circuitry 234 and current driver circuitry 236 of FIG. 2 may share the comparator 426) since generally only one current driver circuitry instantiation is active at a time). Furthermore, comparator 426 may additionally or instead serve as the dropout detecting comparator since $\varepsilon$SUPPLY-driven PCD) feedback is generally not used when dropout detection is used.

The $\varepsilon$TRACK generating comparator 418 uses two identical capacitive dividers to compare the DVS output voltage to the voltage of the electrode that is on the same side of the H-bridge, and the capacitive dividers have sufficient division ratios to protect the comparator inputs from voltages exceeding VDD. The divided down DVS and electrode voltages are being measured from high-impedance nodes, and therefore, these sense signals may be sensitive to charge-injection and capacitive feed-through. Accordingly, each current driver circuitry may have a dedicated $\varepsilon$TRACK generating comparator (e.g. Comparator 418), as to avoid the use of switches that would otherwise link the divider nodes of two instantiations of current driver circuitry if a shared $\varepsilon$TRACK generating comparator was instead employed.

Before (or after) the H-bridge front-end has completed the stimulus delivery state-cycle, the capacitive divider of each current driver circuitry subsystem may be reset, so that each can be forced to known (e.g. identical) operating points between stimulus delivery events. For a given current driver circuitry subsystem, the capacitor dividers may be reset by 1) closing the switch attached to the internal node of each divider (e.g. forcing the internal nodes to ground), 2) connecting the electrode to ground (via low-side switch and the relevant HVA) and 3) discharging the DVS to 0V by placing it in its SINK setting and forwarding pulses to it; this reset can be applied to both current driver circuitry subsystems at some point during State 1 (the "idle" state), described with reference to FIG. 3.

The output of either comparator 418 and/or comparator 426 may be used by the current driver circuitry 402 to gate pulses of the fDVS clock signal, with the resulting signal being Φ, the pulse signal that is forwarded to the DVS. The error signal that is used as the pulse-gating signal may depend on the configuration the current driver circuitry 402 is placed in.

Figure 5:
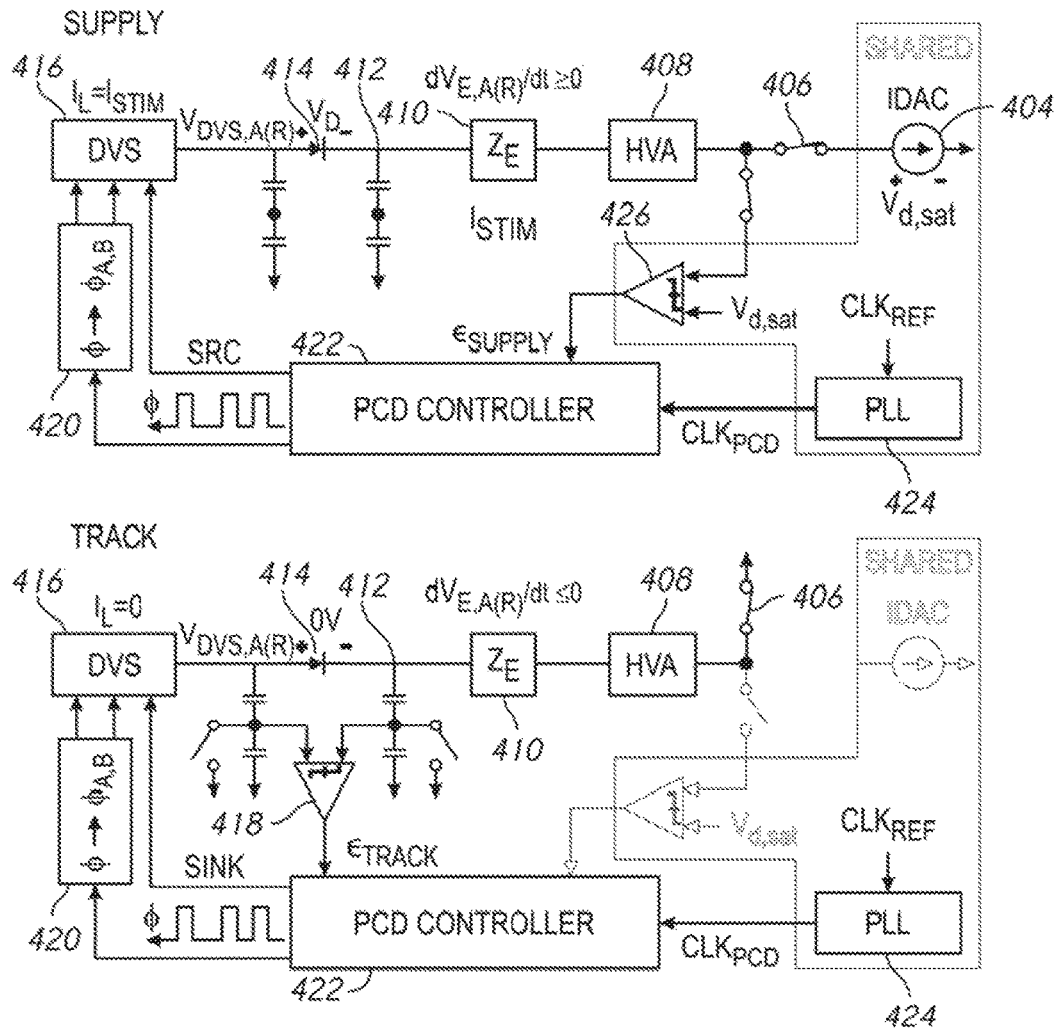
FIG. 5 illustrates schematic examples of two configurations of the current driver circuitry 402 of FIG. 4.

FIG. 5 illustrates schematic examples of two configurations of the current driver circuitry 402 of FIG. 4. The same reference numbers are used for like components.

When placed in the supply configuration the current driver circuitry 402 sets the output voltage of the DVS 416 to keep the voltage across the current DAC 404 approximately equal to a desired set voltage (e.g. Vd,sat) as the current DAC 404 regulates $I_{STIM}$ through impedance 410. As the DVS 416 supplies positive $I_{STIM}$ to the node 412 on the same side of the H-bridge, the DVS 416 will have its output voltage (e.g. $V_{DVS,0/1}$) set high enough (e.g. with respect to $V_{E,0/1}$) to turn the high-side switch 414 (e.g. a diode) ON.

It is known that the load current ($I_{STIM}$) of the DVS 416 will be constant-current and sinking while the current driver circuitry 402 is in this configuration, and to maintain a given output voltage the switched-capacitor-based DVS 416 will have to supply an offsetting average current. Furthermore, by assuming the reactive component of impedance 410 appears capacitive, the voltage measured across impedance 410 may in some examples be assumed to have a derivative (with respect to time) greater or equal to zero (e.g. since $I_{STIM}$ is constant-current). Accordingly, the DVS 416 can be kept in its source setting while in this configuration and fDVS pulses can be gated using εSUPPLY, as to produce a Φ which has an average period that sets the output high voltage to the desired level to keep the current DAC 404 voltage at the $V_{dsat}$ set voltage (on average). This ON/OFF DVS regulation scheme may prevent or reduce instability within the current driver circuitry 402 loop; however, there may be voltage ripple at the DVS output (and subsequently at both electrodes) of predictable and limited magnitude due to the switched-capacitor nature of the DVS 416 and the ON/OFF DVS conduction cycles.

For the DVS 416 to deliver $I_{STIM}$ across its full output voltage range, the frequency of the pregated pulse signal (fDVS) may advantageously be made sufficiently high for the maximum output power condition (e.g. delivering $I_{STIM}$ at $V_{MAX}$).

When placed in the track configuration, the current driver circuitry 402 is not delivering stimulus to node 412 and its associated DVS 416 is unloaded. Meanwhile, on the other side of the H-bridge the low-side of the HVA is set to ground (see state-cycle in FIG. 3). Accordingly, the track configuration may be provided to force $V_{DVS,0/1}$ to be approximately equal to $V_{E,0/1}$, as to keep the switch 414 (e.g. a diode) reliably OFF and to keep HVA 408 biased properly (since $V_{E,0/1}$ may be at any level in the 0V to VMAX range).

The configuration a current driver circuitry instantiation is placed in (e.g. SUPPLY, TRACK) may determine: 1) if the dedicated comparator 418 of the PCD is enabled; 2) which signal is used to gate fDVS pulses into the DVS (e.g. εSUPPLY or εTRACK); 3) which SOURCE/SINK setting the DVS remains fixed in; and 4) whether the capacitive divider reset switches are opened or closed. Furthermore, assuming fDVS can be changed (or multiplexed from a selection of clocks), then each configuration can be provided a tailored fDVS frequency (for a given configuration, it may be useful to run the DVS at a lower maximum frequency than in others).

Figure 6:
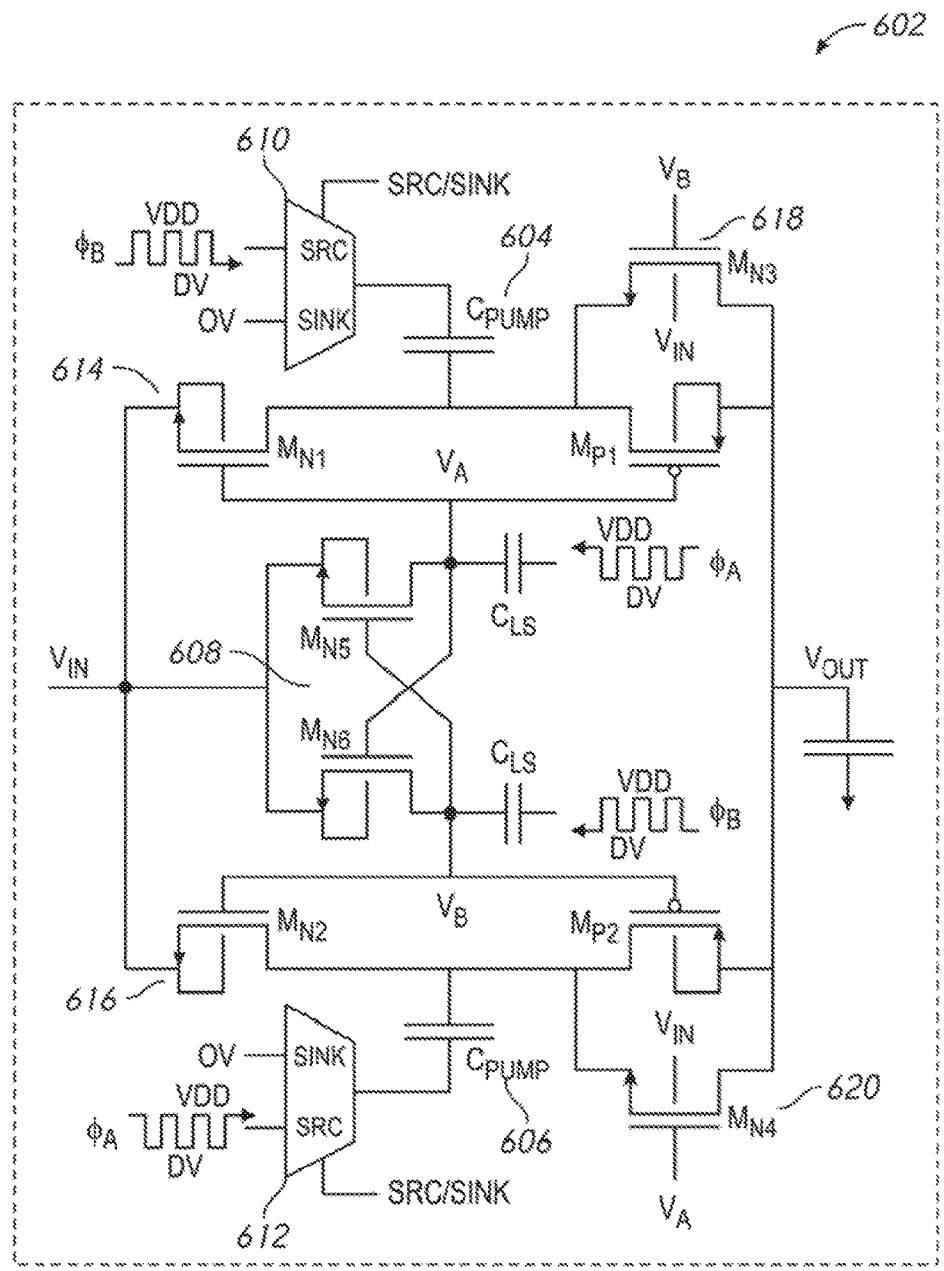
FIG. 6 is a schematic illustration of a stage of a dynamic voltage supply (DVS) circuit arranged in accordance with examples described herein.

FIG. 6 is a schematic illustration of a stage of a dynamic voltage supply (DVS) circuit arranged in accordance with examples described herein. The 'N' subscript is generally used to describe an NMOS device, while the 'P' subscript is generally used to describe a PMOS device. The stage 602 includes a level shifter 608 coupled to a voltage input $V_{IN}$, and switch devices 614 and switch devices 616 coupled to the output of the level shifter 608. The switch devices 614 are coupled to a plate of a pump capacitor Cpump 604. The switch devices 616 are coupled to a plate of a pump capacitor Cpump 606. The other plate of the Cpump capacitors are controlled by multiplexers, multiplexer 610 and multiplexer 612 respectively. An additional transistor 618 is provided in parallel with one of the switch devices 614 and connected to the output $V_{OUT}$. An additional transistor 620 is provided in parallel with one of the switch devices 616 and connected to the output $V_{OUT}$. In this manner, the output $V_{OUT}$ is connected to a parallel combination of NMOS and PMOS transistors.

Dynamic voltage supplies used in current driver circuitry described herein (e.g. DVS 416 of FIG. 4) may be implemented using a multi-stage, switched-capacitor power converter, terminated by a large capacitor ($C_{OUT}$). A single stage 602 of a DVS is shown in FIG. 6 implemented as a modified voltage-doubler, employing two "pumping capacitors" (e.g. Cpump 604 and Cpump 606) to either source (SRC) or SINK switched-capacitor current (with equal drive strength) to and from the output, respectively (for $V_{OUT} \geq V_{IN}$). In current driver circuitry described herein (e.g. see FIG. 4 and FIG. 5), a 1-bit error generated by a low-voltage CMP may be used to gate a high-frequency clock ($CLK_{PCD}$) into the DVS switching signal input (Φ), with the resulting unidirectional feedback (e.g. on/off regulation) ensuring loop stability. The maximum N-stage DVS output voltage ($V_{MAX}$) may be limited only by the reverse-breakdown voltage of the n-well/substrate junction (≈12V for an example CMOS process); this barrier ultimately limits the compliance of the analog front-end circuitry, instead of individual device voltage limits.

A stage 602 of a dynamic voltage supply (DVS) is shown in FIG. 6. One or more stages including the stage 602 may be used to implement dynamic voltage supplies in current driver circuitry described herein, such as the DVS 416 of FIG. 4. The stage 602 may supply switched-capacitor current from $V_{IN}$ to $V_{OUT}$ (SRC) while establishing a voltage difference between $V_{OUT}$ and $V_{IN}$, as well as sink switched-capacitor current in the $V_{OUT}$ to $V_{IN}$ direction (SINK), which may allow for or facilitate the safe and feedback-controlled discharge of the positive-current drivers; for both settings, $0 < V_{OUT} - V_{IN} < VDD$.

In FIG. 6, ΦA,B are complementary pulse/clock signals. Assuming a large output capacitance, the single-stage circuit, operated in both settings, displays the same effective internal resistance; this term is inversely proportional to $C_{PUMP}$ and the ΦA,B frequency, making $V_{OUT}$ linearly related (approx.) to the "pumping period" under constant-current loading. When unloaded, $V_{OUT} - V_{IN}$ can traverse the 0V to $V_{DD}$ span, with rise/fall time determined by the internal resistance and output capacitance; the circuit can maintain $V_{OUT}$ by setting ΦA,B to DC, since there is no load resistor to ground.

Multiplexer 610 and multiplexer 612 are provided and coupled to drive the bottom-plate of the $C_{PUMP}$ capacitors, Cpump 604 and Cpump 606, as opposed to directly driving these nodes with ΦA and ΦB. The use of multiplexer 610 and multiplexer 612 in some examples may allow the direction the switched-capacitor current to be chosen/changed: when in the SOURCE setting, the stage 602 (and DVS) sources, or supplies, switched capacitor current to $V_{OUT}$; when in the SINK setting, the stage 602 (and DVS) sinks, or removes, switched-capacitor current from $V_{OUT}$. Accordingly, when the multiplexer control bit is set accordingly (e.g. could be designated low or high) (e.g. source is the active setting), multiplexer 610 and multiplexer 612 may feed through ΦA and ΦB (e.g. complementary 50% duty cycle pulse signals) to the bottom-plates of Cpump 604 and Cpump 606, and as a result the stage 602 functions as a voltage-boosting power-converter. When instead the multiplexer control bit is set high (SINK is the active setting), multiplexer 610 and multiplexer 612 keep the bottom-plate of the Cpump 604 and Cpump 606 at a reference voltage (e.g. ground). This operation may ultimately provide a multi-stage DVS with the current sinking functionality desired for the safe and controlled discharge of the output capacitance.

The level shifter 608 circuit, including transistor $M_{N5}$, $M_{N6}$, and two capacitors $C_{LS}$, functions to transform the ΦA and ΦB pulse signals into $V_A = \Phi A + V_{IN}$ and $V_B = \Phi B + V_{IN}$, respectively. VA and VB are then applied to the gates of the top-plate switch devices (e.g. Switch devices 614 and switch devices 616 including MN1,2,3,4 and MP1,2). Because all of the gate-driving signals of the DVS circuit are decoupled from the voltage at the top-plate of the $C_{PUMP}$ capacitors, Cpump 604 and Cpump 606, the DVS circuit may be operated in both its SOURCE and SINK settings, while other voltage-doubler topologies may only be able to be operated in a SOURCE-equivalent setting.

Note the switch signals have been decoupled from the $C_{PUMP}$ capacitors Cpump 604 and Cpump 606 via the $M_{N5-6}$ level shifter 608, and the NMOS devices $M_{N3-4}$ may facilitate or allow the complete discharge of the output capacitor under non-loaded conditions. The presence of the transistor 618 (MN3) and transistor 620 (MN4) may also provide some advantages in some examples. When the DVS is in its SINK setting, the transistor 618 and transistor 620 may allow $V_{OUT}$ to be discharged completely to $V_{IN}$ (e.g. if unloaded by a charge supplying source); if the transistor 618 and the transistor 620 were not present, $V_{OUT}$ may not be reliably discharged below $V_{IN}$+Vth,p, where Vth,p is the threshold voltage of the connected devices in the switch devices 614 and switch devices 616 sets (e.g. the MP1 and MP2 devices).

Generally, the stage 602 operates as a voltage doubler circuit. N single-stage DVS circuits can be cascaded in series to generate voltages exceeding $V_{DD}$. For example DVS circuits used in current driver circuitry described herein, $V_{IN}$ of the cascaded chain of stages may be set to ground to enable the desired 0V to $V_{MAX}$ output voltage range during SOURCE-setting operation and to allow $V_{OUT}$ to be discharged down to 0V during SINK-setting operation. To prevent the body-effect from degrading the functionality of the switches as $V_{IN}$ and $V_{OUT}$ of a single-stage circuit increase (e.g. as these voltages would in an N-stage cascade), all NMOS devices shown in stage 602 may be implemented using deep-n-well (DNW) devices and the bodies of the NMOS and PMOS devices may be tied to $V_{IN}$ and $V_{OUT}$, respectively; likewise, the DNW of MN1,2,3,4 may be tied to $V_{OUT}$ while the DNW of MN5 and MN6 are referenced to VB and VA, respectively. Accordingly, in a CMOS process the reverse breakdown voltage of the p-substrate-to-deep-n-well (PSUB/DNW) junction may limit the maximum output voltage that can be generated by a DVS. The output of an N-stage DVS is connected to a large capacitor, $C_{OUT}$, where generally $C_{OUT} \gg C_{PUMP}$ as to reduce the amount of ripple observed at the DVS output.

To create high voltages, several stages such as the stage 602 may be cascaded, with a large output capacitor ($C_{OUT}$) attached to the terminating stage. All NMOS transistors shown in FIG. 6 may be implemented using triple-well devices, allowing local body-biasing to suppress the body effect. The highest voltage ($V_{MAX}$) generated by this circuit is generally limited by the reverse breakdown voltage of the p-sub/n-well junction; for an example 65 nm CMOS process, this limit is approximately 12V. High voltages also make the use of MiM/MoM capacitors for $C_{PUMP}$, $C_{LS}$, and $C_{OUT}$ desirable. To provide 0V to $V_{MAX}$ at the output, the input of the multi-stage supply may be set to a reference voltage (e.g. chip ground); this connection also provides enhanced DC power-supply isolation for the electrodes/tissue.

Figure 7:
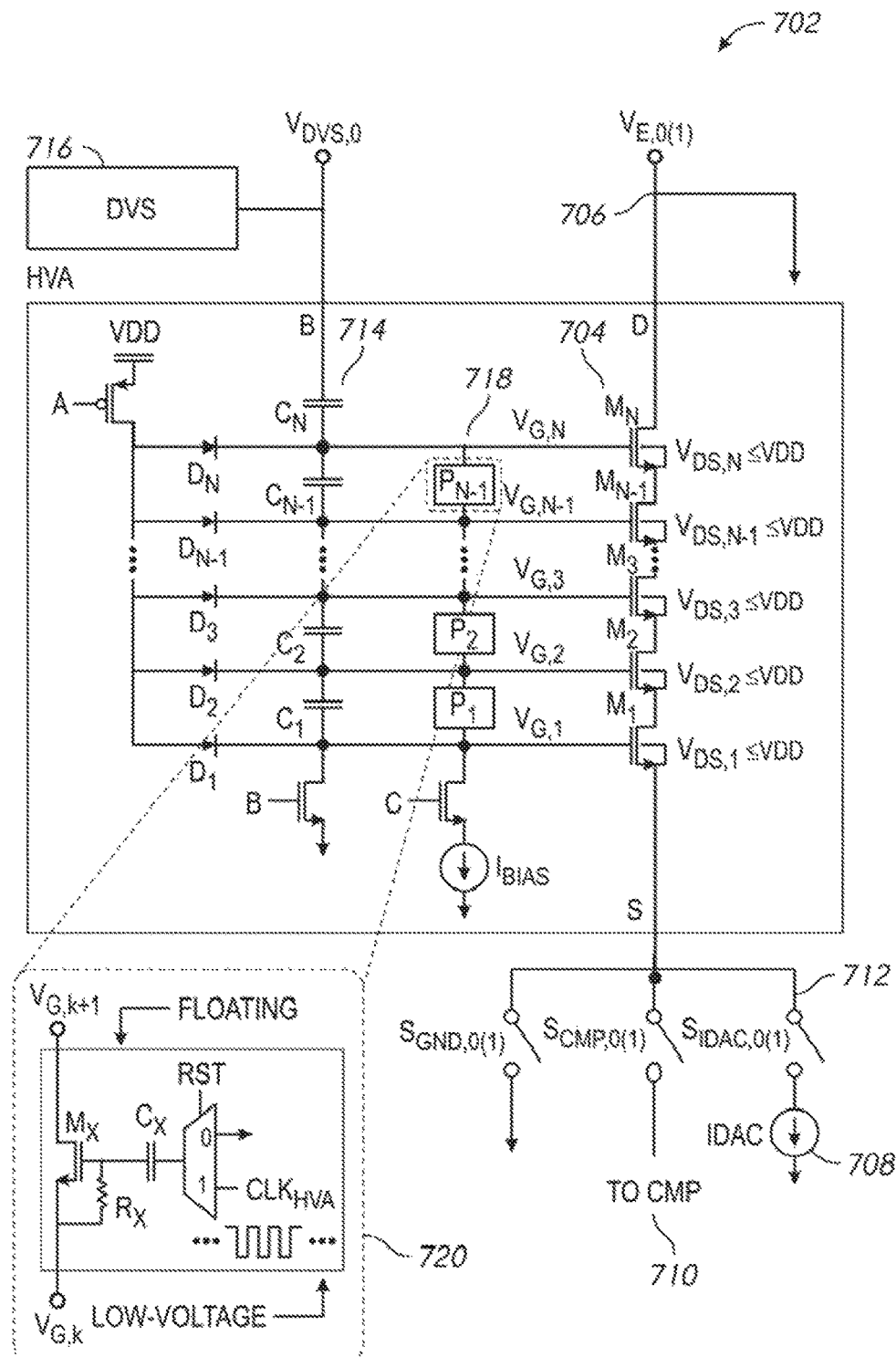
FIG. 7 is a schematic illustration of a high-voltage adapter (HVA) circuit arranged in accordance with examples described herein.

FIG. 7 is a schematic illustration of a high-voltage adapter (HVA) circuit arranged in accordance with examples described herein. The HVA 702 may be used to implement any HVA described herein, such as the HVA 408 of FIG. 4, or the HVA 210 or HVA 212 of FIG. 2. The HVA 702 includes capacitive divider 714 coupled to a DVS. In parallel with the capacitive divider 714 is a series of sub-modules 718. The HVA further includes a transistor cascode 704 coupled between a node 706 and other circuitry or reference voltage (e.g. low voltage circuitry). The other circuitry, may be for example, a reference voltage (e.g. ground), a comparator 710, or a DAC 708. Switches 712 are provided to make connections between the transistor cascode 704 and the reference voltage, comparator 710, and/or DAC 708.

A number of stages in the HVA 702 (e.g. number of transistors in the transistor cascode 704 and capacitors in the capacitive divider 714) may be set in accordance with the voltage rating of the devices used to implement each stage (e.g. $V_{DD}$) and the maximum voltage the HVA 702 is expected to interface with (e.g. $V_{OUT}$(max)).

The node 706 may be implemented as, or in electrical communication with, a stimulus or return electrode as described herein. The node 706 may be used to implement, or may be implemented as, for example the node 412 of FIG. 4 or the node 206 or node 204 of FIG. 2.

The transistor cascode 704 may be implemented using equally-sized deep-n-well NMOS devices (e.g. transistors) to provide a safe conduction pathway between node 706 (which may be at high voltages) and low-voltage circuits (e.g. a reference voltage, such as ground, a comparator 710, or DAC 708), switches 712 may be provided to connect one or more of a reference voltage, comparator 710, or DAC 708 to the transistor cascode 704. The comparator 710, reference voltage, DAC 708, and switches 712 may be used to implement, or may be implemented as, the comparator, reference voltage, DAC, and/or switches described herein, for example, with reference to FIG. 2 and FIG. 4 (e.g. Current DAC 208).

The capacitive divider 714 may provide a device-protecting gate-biasing function, which may ensure or aid in ensuring that when large electrode voltages are generated, each transistor in the transistor cascode 704 does not experiences terminal-to-terminal voltage exceeding the device Von-rating. The capacitive divider 714 includes a plurality of capacitors coupled in series, each capacitor provided between a gate of a transistor in the transistor cascode 704 and a next capacitor in the capacitive divider 714. An end of the capacitive divider 714 is coupled to the DVS 716 which may be implemented using any DVS described herein, including the DVS 416 of FIG. 4 or the DVS 716 of FIG. 7.

The capacitors in the capacitive divider 714 may be sized to apply a gate-biasing function to the gates of the transistors in the transistor cascode 704. CN, the top-most capacitor in the stack, may be sized to make sure the constant-gain term, α (e.g. $V_{G,N}/V_E$), falls within a safe" range of values that provides $V_{DS}$ and $V_{GS}$ reliability throughout the HVA device stack as the voltage at the node 706 varies between 0V and its expected maximum value. Accordingly, in sizing CN the effective capacitance in-series with it may desirably be known, as well as the worst-case "PCD error ratio" (e.g. $V_{max}/V_E$) when the current driver circuitry controlling the HVA-biasing DVS 716 is SUPPLY-configured (error ratio greater than 1 due to diode high-side switch) and TRACK-configured (error ratio potentially less than 1).

CN−1 through C1 are sized to realize a capacitive divider with constant-increment voltage division, as to provide the "k" and "N" dependent component of the HVA gate-biasing function.

When the HVA 702 is ACTIVE (e.g. stimulus is being delivered), the bottom of the capacitive divider 714 may be maintained at $V_{ON}=V_{DD}-V_{D1}$ by $I_{BIAS}$, limiting the voltage at the effective "source" of the HVA 702 to $V_{ON}-V_{GS,1}<VDD$. Meanwhile, the top of the capacitive divider 714 may be biased by the DVS 716 on the same side of the H-bridge as the HVA 702; accordingly, when large electrode voltage variations occur, the electrode and biasing DVS voltages will be approximately equal via current driver circuitry feedback operation. The capacitive divider 714 distributes the DVS 716 output voltage among the gates of a transistor cascode 704; this gate-biasing function may protect the HVA devices from voltage overstress.

Sub-modules 718 may be provided in parallel with the capacitive divider 714 and transistor cascode 704. The sub-modules may be used to reset the HVA capacitive divider between biphasic stimulus pulses. An individual subcircuit 720 that may be used to implement each of the sub-modules 718 is also shown in FIG. 7, and includes a transistor (Mx), a resistance between the gate and source of the transistor, and a capacitance between the gate of the transistor and a multiplexer which may provide either a reset signal or a clock signal. Accordingly, the Mx device in-parallel with capacitors in the capacitive divider 714 is normally off, unless AC coupled pulses are forwarded by the multiplexer to repeatedly open and close MX, as to discharge the in-parallel capacitor over the course a few pulse cycles. In this manner, the capacitive divider may be considered to divide absolute V by resetting all nodes to a reference voltage (e.g. 0V) between stimulus pulses So there isn't charge build-up/deviation over time, this may be performed between each stimulus pulses event. During stimulation, the output of the multiplexer may be DC, and the gate of a given MX device may follow its source voltage (e.g. via RX resistor) . . . and during HVA reset, in which no stimulation is occurring and electrode/dvs voltages may be known to be a reference voltage (e.g. 0V), clock pulses may be passed through the multiplexer and AC coupled to the gates of the MX devices, switching them on/off and discharging each cap in the divider to 0V over a few clock cycles. In this manner, a capacitive divider may be reset using low-voltage devices. The AC coupling caps may be MiM or MoM caps to hold a high voltage. The low-duty cycle of neural stimulation (typically <<50%) may be leveraged to reset the HVA 702 between stimulus events, during which the DVS 716 and electrode voltages (e.g. at node 706) are known to be 0V (e.g. State 1 in FIG. 3). To quickly reset the HVA 702, $V_{DD}$ and $I_{BIAS}$ may be disconnected, the bottom-plate of C1 may be grounded, and pulses are AC-coupled to the gates of the transistor cascode 704 devices to discharge C1 through CN−1. An HVA 702 can be placed in standby by disconnecting $I_{BIAS}$; this configuration may be useful in keeping an electrode connected to ground during any long intervals between stimulus events (while the HVA 702 consumes no or negligible power).

Figure 8:
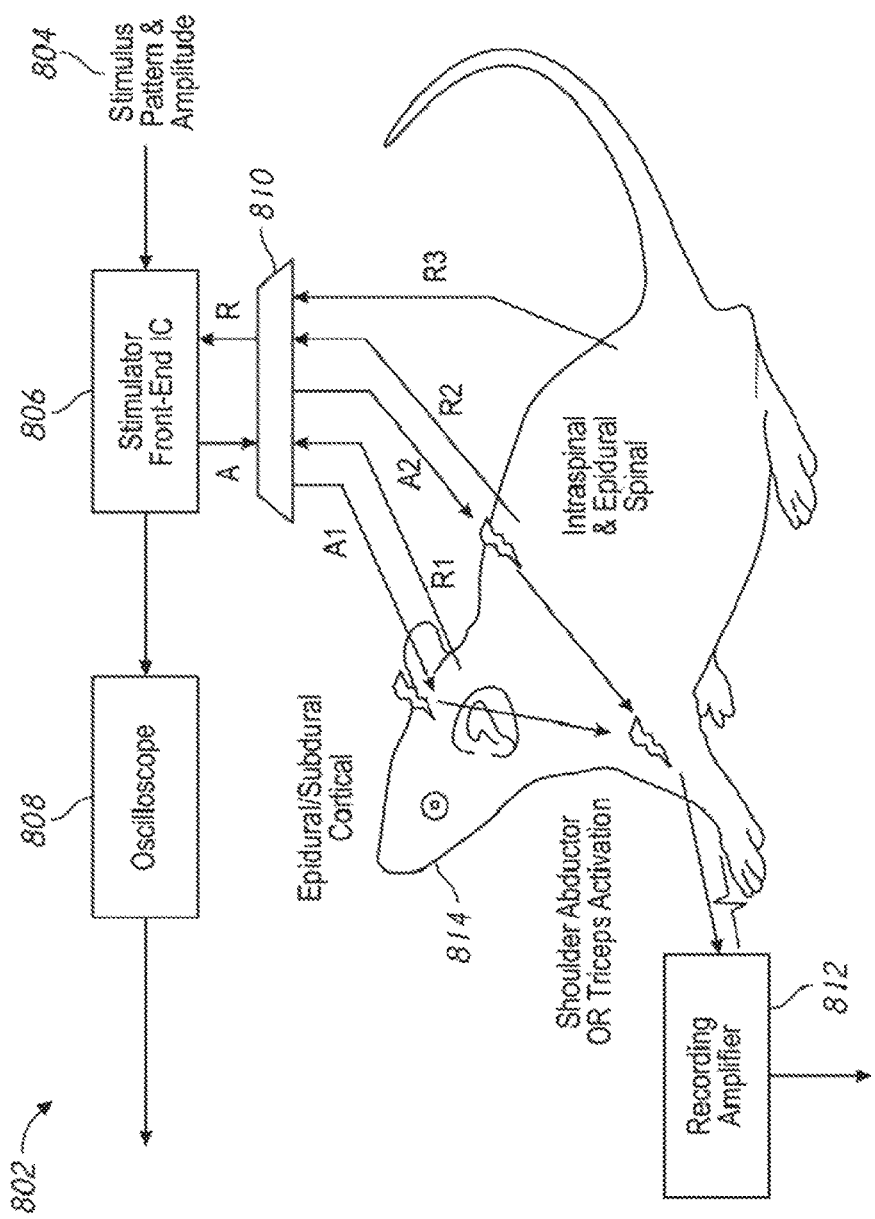
FIG. 8 is a schematic illustration of a system arranged in accordance with examples described herein.

FIG. 8 is a schematic illustration of a system arranged in accordance with examples described herein. The system 802 includes stimulus pattern 804, analog front-end circuitry 806, display 808, MUX 810, amplifier 812, and animal 814. The stimulus pattern 804 may be provided to the analog front-end circuitry 806, which may generate stimulus signals, including biphasic constant-current stimulus signals in accordance with the stimulus pattern 804. The stimulus signals may be provided to MUX 810 for distribution to one or more electrodes implanted or in communication with locations of tissue of an animal 814. Stimulus signals may be viewed on display 808, such as an oscilloscope. An amplifier 812 may be used to receive and/or process signals detected from the animal 814 responsive to the stimulus signals.

The analog front-end circuitry 806 may be implemented using any analog front-end circuitry described herein, including but not limited to analog front-end circuitry 108 or analog front-end circuitry 202. The analog front-end circuitry 806 may be implemented on a chip, and may be fabricated on the same chip as digital logic circuitry used to implement communication with display 808, stimulus pattern 804, and/or amplifier 812. Moreover, portions or all of the stimulus pattern 804 generating logic, and/or the amplifier 812 may be provided on a same chip as the analog front-end circuitry 806 and may be fabricated in a same CMOS process. The chip may be implanted, placed on, or otherwise in communication with tissue of the animal 814.

The stimulus signal generated by the analog front-end circuitry 806 may be provided to electrodes in contact with various tissue locations of the animal 814. In the example of FIG. 8, an electrode A1 is implemented as a silver ball electrode at a forelimb area of a motor cortex of the animal 814. Electrode R1 is implemented as a skull-screw return electrode. Electrode A2 and R2 are implemented as Pt/Ir wires in a cervical spinal cord of the animal 814. Electrode R3 is implemented as a stainless steel dorsal return electrode. In this manner, cortical, spinal, and muscle signals may be delivered and received by the system 802.

While a MUX 810 is shown in FIG. 8 to route a stimulus signal to desired electrodes, in some examples, sufficient analog front-end circuitry may be provided to support multiple parallel channels for stimulus signals. Accordingly, MUX 810 may not be needed in some examples.

Stimulus signals may be provided to, and responsive signals received from, any of a variety of animals in accordance with examples described herein. While a rat is shown implementing the animal 814 in FIG. 8, any animal may be used including, but not limited to, human, cat, dog, mouse, guinea pig, pig, horse, cow, chicken, monkey, ape, fish, or combinations thereof.

Chips, circuits, systems, and/or devices described herein may be used to provide electrical stimulation in any of a variety of devices or systems including, but not limited to, retinal and cochlear implants, deep brain stimulation for Parkinson's disease and neuropsychiatric disorders, functional electrical stimulation of periphery nerves, neural-recording brain-computer interfaces (BCIs), or combinations thereof. For example, neural stimulation could be used as a direct means of closing the "BCI loop" to create "bidirectional" BCIs (e.g. BBCIs) and/or re-establishing brain control over paralyzed muscles.

Example 1

Chip Measurements

A 6-stage dynamic voltage supply (DVS) was fabricated in 65 nm CMOS. The 2.5V devices of the process were used to implement the circuit. CPUMP and COUT of the DVS were 2 pF and 75 pF, respectively, and the switching devices were sized for 400 MHz (max.) operation. The supply rise/fall time under non-loaded conditions showed the ability to track quickly changing electrode voltages; a "faster" supply, operated at the same frequency, can be realized by making CPUMP larger and/or COUT smaller.

Loaded performance (constant-current), output voltage versus ΦA,B period (both measured and predicted) was reviewed; the prediction was derived from a model of the supply internal resistance. A difference in slope between the predicted/measured SRC curves was attributed to reverse leakage current due to ΦA, ΦB overlap; the result was reduced efficiency (an improved non-overlapping clock may mitigate this issue).

Biphasic Driver Simulations

A biphasic driver designed for 250 µA stimulus delivery (max.) and ±11V compliance was implemented at the schematic level in Cadence; potential uses include intracortical and intraspinal stimulation. The IDAC had an ROUT of 500 kΩ; the high frequency supply clock was 125 MHz, and error detection circuitry (using non-ideal comparator model) was operated at 25 MHz; all other blocks are implemented at the transistor level. The voltage across $Z_E$ was observed for several "high-impedance" interfaces, when 250 µA biphasic current (200 µs pulse-width, 5 µs interphase delay) was delivered. System performance, for a "worst-case" stimulus rate of 1 kHz, was reviewed.

The stimulator demonstrated adequate stimulus current regulation, and although HVA mismatches are not simulated, the DC stimulus mismatch, just by using fixed-duration passive/active discharge phases post-stimulus, was below 100 nA for ZE1-4.

Considering relative stimulus levels and duty cycles, the power consumption was comparable to systems featuring a static high voltage rail (which also needs to be generated) and high voltage tolerant devices. A system with similar performance can be designed for higher current levels by increasing the clock frequency of the supply/error-detection and/or increasing the CPUMP size.

In-Vivo Board Testing

A board-level prototype was realized to investigate potential uses for the integrated stimulator (considering its ±11V compliance), and to verify the current regulating ability of an H-bridge driver in-vivo. The board used discrete, high-voltage tolerant components and was operated by a micro-controller, charge balance was assured by the inclusion of large blocking capacitors; the fabricated DVS chip was not used in this system. Two rats, previously surgically implanted with several electrode configurations (subdural cortical, intraspinal, and intramuscular) were stimulated while moving freely about an observation area. The stimulator board was connected to the electrodes with a tethered cable. A 300 µm multi-stranded, stainless steel (SS) wire was used for the current return, and the active electrode was either a 300 µm multi-stranded SS wire (intramuscular, cortical) or 30 µm Pt/Ir (intraspinal). Electromyographic (EMG) responses in the muscle and spinal cord (latter for cortical stimulation) were recorded during stimulus delivery. Sufficient current was delivered to cortical, spinal, and muscle electrodes to evoke forelimb or neck contractions.

ZE voltage at movement-eliciting current levels (verified visually and with EMG) was demonstrated for intramuscular stimulation (SS active/return wires in close proximity; ZE voltages for subdural cortical stimulation (distant SS return) also stayed within the capabilities of the stimulator. Responses were also provoked with spinal stimulation (distant SS return), and with lower ZE driving voltages.

Example 2

Analog front-end circuitry was fabricated in the 9-metal, TSMC 65 nm GP CMOS process. ±11V to ±10V compliance was measured when delivering biphasic stimulus current ranging from 50 µA to 2 mA in amplitude, respectively.

Chip Implementation and Overview

The active chip area was ≈2 mm². The DVS design used 8-stages and a 2.5V VDD, with CPUMP and COUT set to 13.1 pF and 180 pF, respectively. The maximum frequency of CLKPCD was 8×13.56 MHz but lower multiples of 13.56 MHz (e.g. ×4, ×2, and ×1) can be used in other examples based on the stimulus amplitude setting.

The HVA employed 7-stages, with C1 through C7 set to ensure the terminal-to-terminal voltages of each cascoded device stayed within ±2.5V during high-voltage stimulation. The chip used 3 clocked-comparators (CMPs), each having the same design and a maximum sampling rate of 8×13.56 MHz. Each current driver circuitry instantiation (e.g. PCD) had a dedicated CMP for TRACK-feedback error detection, and the third CMP was used for current DAC dropout detection and shared by both PCDs for SUPPLY-feedback error detection. The low-voltage, binary-weighted IDAC had a 10 µA LSB and featured a 2.5V-tolerant active-cascode buffer. An on-chip phase-locked loop (PLL) took a 13.56 MHz input (ISM band) from off-chip and generated the high-frequency clocks used by the CMPs, DVSs, and HVAs. An off-chip micro-controller generated a 200 kHz system clock and a 4-bit bus which encoded the "state" of the front-end; this bus was input to a large multiplexing structure, which then forwarded the correct configuration codes (e.g. all scanned into the chip) to the front-end blocks, digitally guiding the chip through each state of stimulus delivery.

Benchtop Stimulator Front-End Measurements

PCD voltages and ZE current were measured during high-voltage, 2 mA stimulation with varied ZE. The residual voltage measured after 2 mA stimulus was delivered to the capacitive ZE,2 (for which the front-end functions the most asymmetrically) corresponds to 22 nC of charge-mismatch. When stimulating the purely resistive ZE,3 at a high rate (e.g. 300 Hz) the chip consumed 9.33 mW (nearly all drawn from the 2.5V supply); as ZE becomes more capacitive, this power draw reduces since a larger fraction of the balancing stimulus is not actively supplied by a DVS. The stand-by power consumption of the chip was measured at 304 µW (e.g. leakage, system clocking, comparator biasing, op-amp biasing in IDAC, and charge-pump/VCO biasing in PLL);

the only stand-by power consumption from the high-voltage front-end circuits (e.g. DVSs and HVAs) is a single, 2 µA HVA bias current.

In Vivo Measurements

The in vivo efficacy of the chip was demonstrated by producing motor evoked potentials and overt movement in the triceps and shoulder abductor of an anesthetized rat through spinal stimulation (intraspinal, epidural) and cortical stimulation (epidural, subdural); four applications relevant to bidirectional neural interface research and development.

From the foregoing it will be appreciated that, although specific embodiments of the invention have been described herein for purposes of illustration, various modifications may be made without deviating from the spirit and scope of the invention.

What is claimed is:

1. Analog front-end circuitry comprising:
    a first current driver circuit comprising a first switched-capacitor power supply configured to produce a first high voltage;
    a second current driver circuit comprising a second switched-capacitor power supply configured to produce a second high voltage; and
    a first switch between the first current driver circuit and a first node;
    a second switch between the second current driver circuit and a second node;
    a first high voltage adapter circuit coupled to the first node;
    a second high voltage adapter circuit coupled to the second node;
    a current digital-to-analog converter (DAC);
    a third switch between the first high voltage adapter circuit and the current digital-to-analog converter;
    a fourth switch between the second high voltage adapter circuit and the current digital-to-analog converter;
    a fifth switch between the first high voltage adapter circuit and a reference voltage;
    a sixth switch between the second high voltage adapter circuit and the reference voltage;
    wherein the first current driver circuit and the second current driver circuit are configured to control at least some of the first, second, third, fourth, fifth, and sixth switches to provide a biphasic voltage signal between the first and second node.

2. The circuitry of claim 1 further comprising:
    a seventh switch between the first high voltage adapter circuit and a voltage comparator; and
    an eight switch between the second high voltage adapter circuit and the voltage comparator;
    wherein the first current driver circuit and the second current driver circuit are configured to control at least some of the first, second, third, fourth, fifth, sixth, seventh, and eighth switches to provide the biphasic voltage signal.

3. The circuitry of claim 2, wherein the first current driver circuit and the second current driver circuit are together configured to control the first, second, third, fourth, fifth, sixth, seventh, and eighth switches to:
    in a first state, provide the reference voltage at both the first and second nodes by disconnecting the first and second nodes from the first and second high voltages;
    in a second state, connect the second current driver circuit to the first node to provide the second high voltage to the first node, connect the second high voltage adapter circuit to the current DAC, and disconnect the first high voltage adapter circuit from the current DAC and the reference voltage;
    in a third state, disconnect the first node from the second current driver circuit, connect the second high voltage adapter circuit to the reference voltage, and connect the first high voltage adapter circuit to the voltage comparator;
    in a fourth state, connect the first high voltage adapter circuit to the reference voltage, connect the second high voltage adapter circuit to the current DAC and the voltage comparator;
    in a fifth state, connect the first current driver circuit to the second node to provide the first high voltage to the second node, connect the first high voltage adapter circuit to the current DAC; and
    in a sixth state, disconnect the second node from the first current driver circuit, connect the first high voltage adapter circuit to the reference voltage.

4. The circuitry of claim 3, wherein the first current driver comprises a first controller configured to cycle through the first, second, third, fourth, fifth, and sixth states, and wherein the second current driver comprises a second controller configured to cycle through the first, second, third, fourth, fifth, and sixth states.

5. The circuitry of claim 1, wherein the first node is configured to couple to a stimulus electrode, and wherein the second node is configured to couple to a reference electrode.

6. The circuitry of claim 1, wherein the first switched-capacitor power supply and the second switched-capacitor power supply comprise transistors configured for operation with a first power supply voltage and wherein the first and second high voltages are at least twice the first power supply voltage.

7. The circuitry of claim 1, wherein the first current driver circuit and the second current driver circuit each comprise a clocked controller.

8. The circuitry of claim 1, wherein the first current driver circuit and the second current driver circuit each are operable in two modes including a first mode configured to provide operation during supply of the first or second high voltages and a second mode configured to track voltage of the first or second nodes during discharge.

9. Circuitry for delivering a biphasic stimulus signal, the circuitry comprising:
    a current source and a plurality of high voltage adapter circuits arranged in an H-bridge topology;
    a plurality of dynamic voltage sources configured to provide voltages for the biphasic stimulus signal, wherein the plurality of states includes a first state providing a negative stimulus, a second state providing an interphase delay, a third state providing a positive stimulus through impedance discharge, and a fourth state providing a positive stimulus through current driver circuitry; and
    a controller configured to cycle the H-bridge topology and plurality of dynamic voltage sources through a plurality of states to provide the biphasic stimulus signal.

10. The circuitry of claim 9, wherein the plurality of states further includes an idle state and an impedance discharge state.

11. The circuitry of claim 9, wherein the circuitry further comprises switches and wherein the controller is configured to open and close the switches to cycle through the plurality of states.

12. The circuitry of claim 9, wherein the controller comprises a digital state machine.

* * * * *